(12) United States Patent
Dey et al.

(10) Patent No.: US 10,870,852 B2
(45) Date of Patent: Dec. 22, 2020

(54) COMPOSITIONS AND METHODS FOR TREATING DIABETIC RETINOPATHY

(71) Applicant: University of Virginia Patent Foundation, Charlottesville, VA (US)

(72) Inventors: Bijan K. Dey, Slingerlands, NY (US); Paul Andrew Yates, Charlottesville, VA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 0 days.

(21) Appl. No.: 15/765,736

(22) PCT Filed: Oct. 6, 2016

(86) PCT No.: PCT/US2016/055812
§ 371 (c)(1),
(2) Date: Apr. 4, 2018

(87) PCT Pub. No.: WO2017/062659
PCT Pub. Date: Apr. 13, 2017

(65) Prior Publication Data
US 2019/0093106 A1 Mar. 28, 2019

Related U.S. Application Data

(60) Provisional application No. 62/237,883, filed on Oct. 6, 2015.

(51) Int. Cl.
*C12N 15/11* (2006.01)
*C07H 21/02* (2006.01)
(Continued)

(52) U.S. Cl.
CPC .......... *C12N 15/113* (2013.01); *A61K 9/0048* (2013.01); *A61K 31/7088* (2013.01);
(Continued)

(58) Field of Classification Search
CPC ................ C12Q 1/6883; C12N 15/113; C12N 2310/113; C12N 2310/315;
(Continued)

(56) References Cited

U.S. PATENT DOCUMENTS

2009/0220589 A1 9/2009 Trieu
2012/0244618 A1 9/2012 Hatzigeorgiou
(Continued)

FOREIGN PATENT DOCUMENTS

EP 3359553 8/2018
WO WO 2004/106356 12/2004
(Continued)

OTHER PUBLICATIONS

The American Heart Association. Coronary Microvascular Disease (MVD). Downloaded on Dec. 4, 2019 from https://www.heart.org/en/health-topics/heart-attack/angina-chest-pain/coronary-microvascular-disease-mvd.*
(Continued)

*Primary Examiner* — Terra C Gibbs
(74) *Attorney, Agent, or Firm* — Jenkins, Wilson, Taylor & Hunt, P.A.; Rodney L. Sparks

(57) ABSTRACT

The application discloses compositions and methods for preventing and treating diabetic retinopathy. It is disclosed herein that an inhibitor of microRNA-let-7b administered to the eye of a subject in need thereof is useful for preventing and treating several problems associated with diabetic retinopathy and plays a role in vasculature stabilization, increasing retinal thickness, reducing retinal capillary dropout, diminishing microvascular leakage, preventing or treating hyperproliferation of microvascular cells, and stabilizing aberrant neovascularization. The invention includes the use of various kinds of inhibitors of microRNA-let-7b, including, but not limited to, an antagomir of miRNA-let-7b. A
(Continued)

useful compound of the invention can be administered into the eye, including intravitreally. A useful antagomir is Dy547-mA(*)mA(*)mCmCmAmCmAmCmAmAmCmC-mUmAmCmUmAmCmCmU(*) mC(*)mA (*)(3'-Chl).

24 Claims, 14 Drawing Sheets
(12 of 14 Drawing Sheet(s) Filed in Color)

Specification includes a Sequence Listing.

(51) Int. Cl.
    C07H 21/04       (2006.01)
    A61K 48/00       (2006.01)
    C12N 15/113      (2010.01)
    A61K 31/7088     (2006.01)
    C12Q 1/6883      (2018.01)
    A61K 31/7125     (2006.01)
    A61K 9/00        (2006.01)

(52) U.S. Cl.
    CPC ........ *A61K 31/7125* (2013.01); *C12Q 1/6883* (2013.01); *C12N 2310/113* (2013.01); *C12N 2310/315* (2013.01); *C12N 2310/321* (2013.01); *C12N 2310/322* (2013.01); *C12N 2310/3231* (2013.01); *C12N 2310/3515* (2013.01); *C12N 2310/3517* (2013.01); *C12N 2320/32* (2013.01); *C12Q 2600/106* (2013.01); *C12Q 2600/158* (2013.01); *C12Q 2600/178* (2013.01)

(58) Field of Classification Search
    CPC ...... C12N 2310/322; C12N 2310/3231; C12N 2310/3515; A61K 31/7088
    See application file for complete search history.

(56) References Cited

U.S. PATENT DOCUMENTS

| 2013/0065951 A1 | 3/2013 | Shen |
| 2013/0216605 A1 | 8/2013 | Mohapatra |
| 2014/0323551 A1 | 10/2014 | Chung |

FOREIGN PATENT DOCUMENTS

| WO | WO 2005054494 | 6/2005 | |
| WO | WO 2007/019107 | 2/2007 | |
| WO | WO 2007/030652 | 3/2007 | |
| WO | WO 2007/089798 | 8/2007 | |
| WO | WO-2007112753 A2 * | 10/2007 | ........... C12N 15/113 |
| WO | WO 2008/060374 | 5/2008 | |
| WO | WO 2010/120969 | 10/2010 | |
| WO | WO 2012/056282 | 5/2012 | |

OTHER PUBLICATIONS

Zhou et al. (Molecular and Cellular Biology, 2017 vol. 37, Issue 16, pp. 1-14).*

Cunha-Vaz, "Diabetic retinopathy: surrogate outcomes for drug development for diabetic retinopathy," Ophthalmologica, 2000, 214, 6, pp. 377-380, Published by Karger Publishers, Basel, Switzerland.

Janssen et al, "Treatment of HCV infection by targeting microRNA," N Engl J Med, 2013, 368, 18, pp. 1685-1694, Published by Massachusetts Medical Society, United States.

Li et al, "Therapeutic targeting of microRNAs: current status and future challenges," Nat Rev Drug Discov, 2014, 13, 8, pp. 622-638, Published by Nature Publishing Group, United Kingdom.

Motiejunaite et al, "Pericytes and ocular diseases," Experimental Eye Research, 2008, 86, 2, pp. 171-177, Published by Elsevier, Amsterdam, Netherlands.

Rakoczy et al, "Characterization of a mouse model of hyperglycemia and retinal neovascularization," Am J Pathol, 2010, 177, 5, pp. 2659-2670, Published by Elsevier, Amsterdam, Netherlands.

Robinson et al, "Update on animal models of diabeti retinopathy: from molecular approaches to mice and higher mammals," Dis Model Mech,2012, 5, 4, pp. 444-456, Published by the Company of Biologists, United Kingdom.

Traktuev et al, "A population of multipotent CD34-positive adipose stromal cells share pericyte and mesenchymal surface markers, reside in a periendothelial location, and stabilize endothelial networks," Cicr Res, 2008, 102, 1, pp. 77-85 (23 pages w/ Online Data Supplements), Published by Lippincott Williams & Wilkins, United States.

Chen et al., "FGF Regulates TFG-B Signaling and Endothelial-to-Mesenchymal Transition via Control of let-7 miRNA Expression," Cell Reports, vol. 2, pp. 1684-1696 (2012).

Extended European Search Report corresponding to International Patent Application No. PCT/US2016/055812 dated Dec. 30, 2016.

International Preliminary Report on Patentability (Chapter 1) corresponding to International Patent Application No. PCT/US2016/055812 dated Apr. 10, 2018.

International Search Report corresponding to International Patent Application No. PCT/US2016/055812 dated Dec. 30, 2016.

Karlin and Altschul, "Applications and statistics for multiple high-scoring segments in molecular sequences," Pro. Natl. Acad. Sci USA vol. 90, pp. 5873-5877 (1993).

Klein et al., "Heredity and age related macular degeneration.," Observations in monozygotic twins. Archives of Opthalmology, vol. 112, No. 7, pp. 932-7 (1994).

Office Action corresponding to European Patent Application No. 16854346 dated Jun. 12, 2020.

Written Opinion corresponding to International Patent Application No. PCT/US2016/055812 dated Dec. 30, 2016.

* cited by examiner

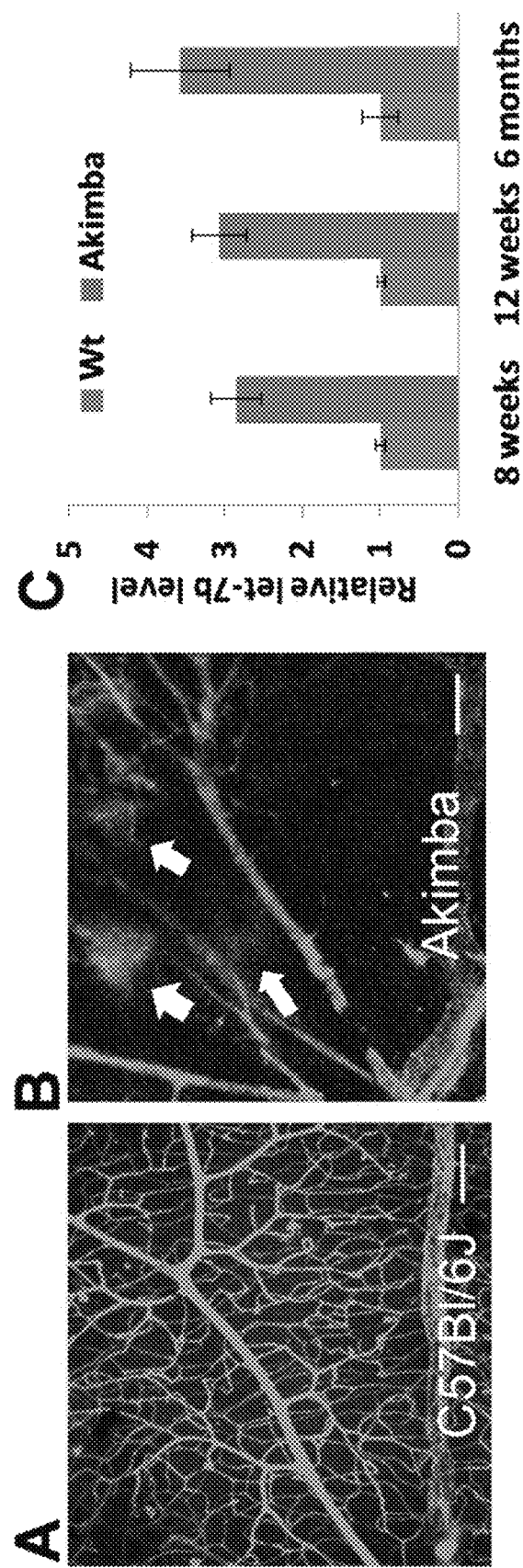
FIG. 3 A-C

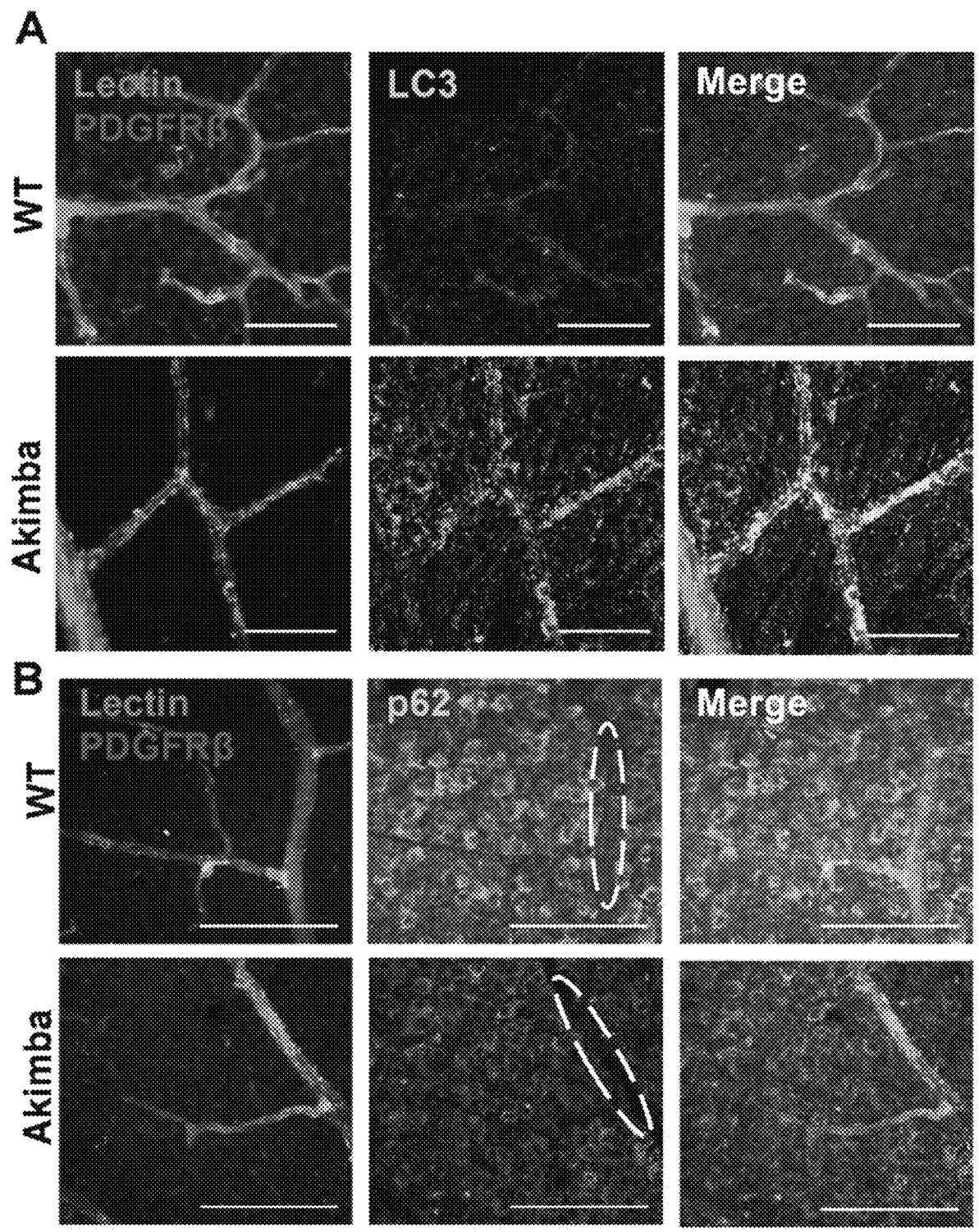
FIG. 4 A-B

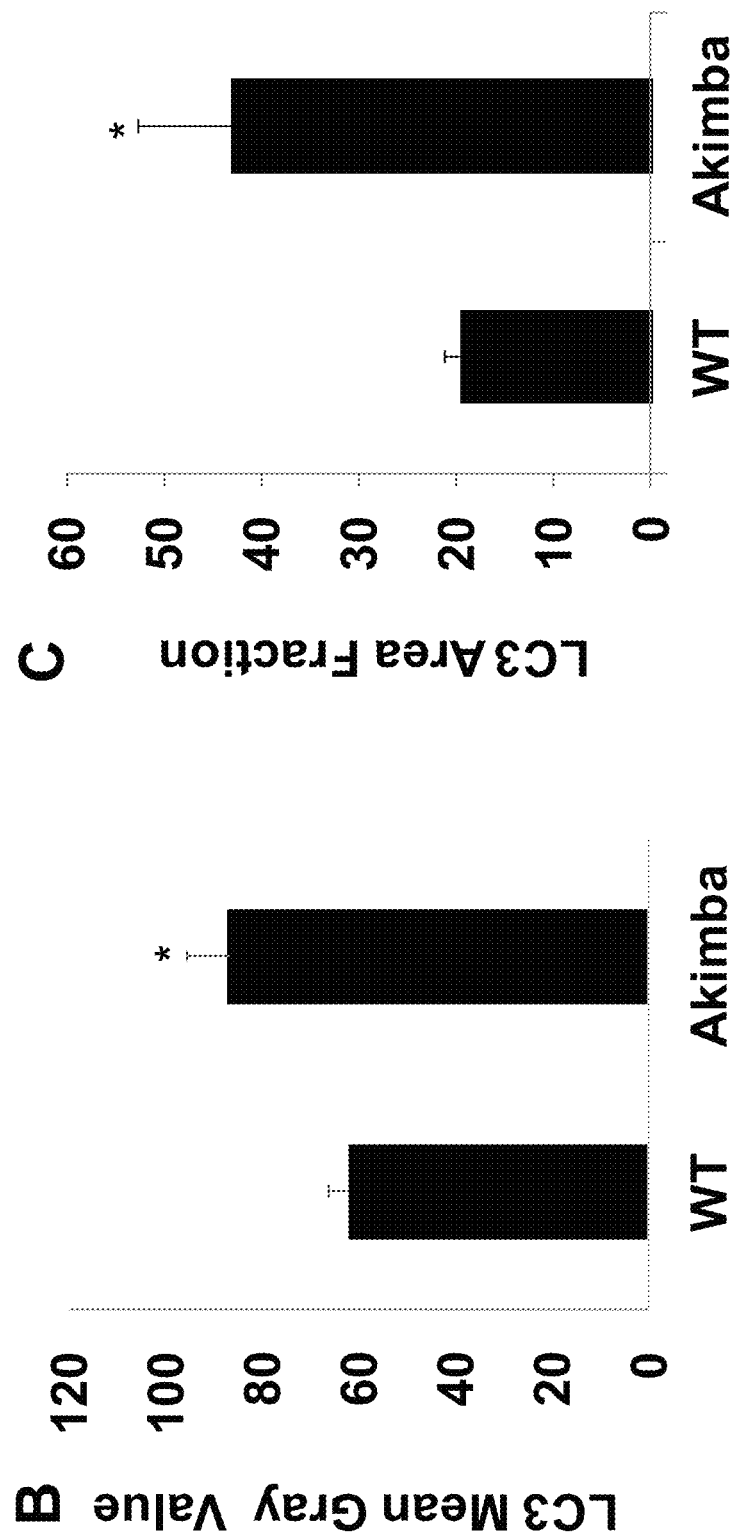
FIG. 5 B-C

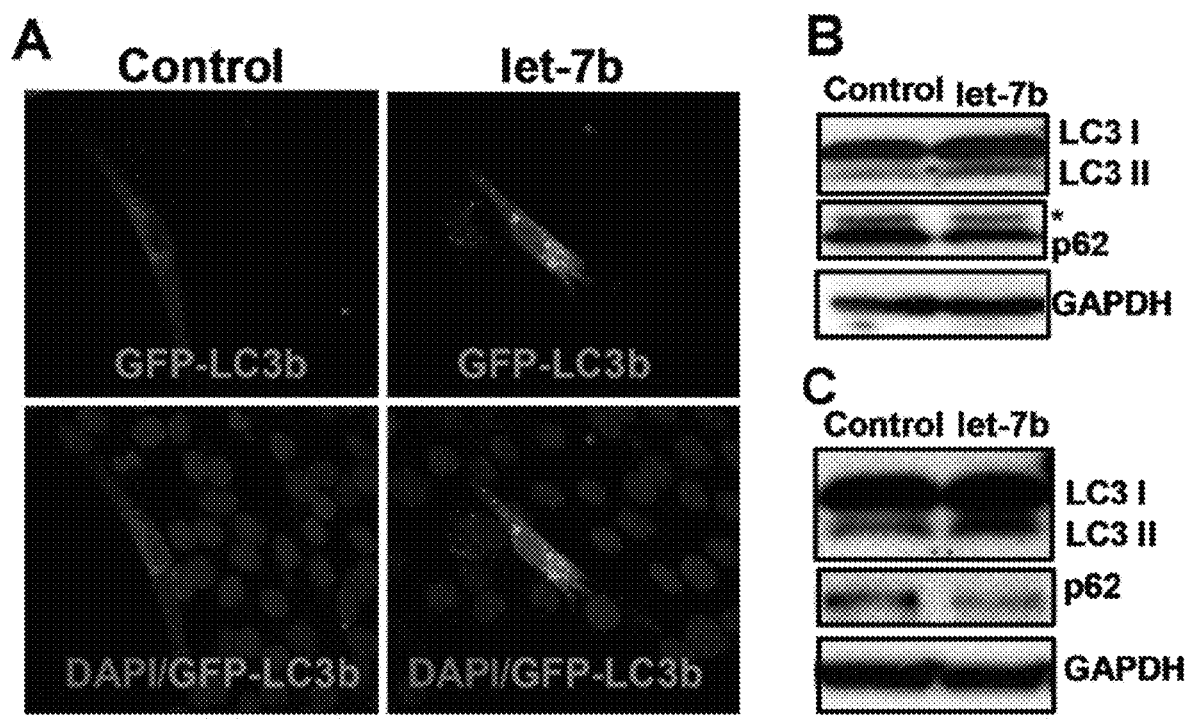
FIG. 6 A-C

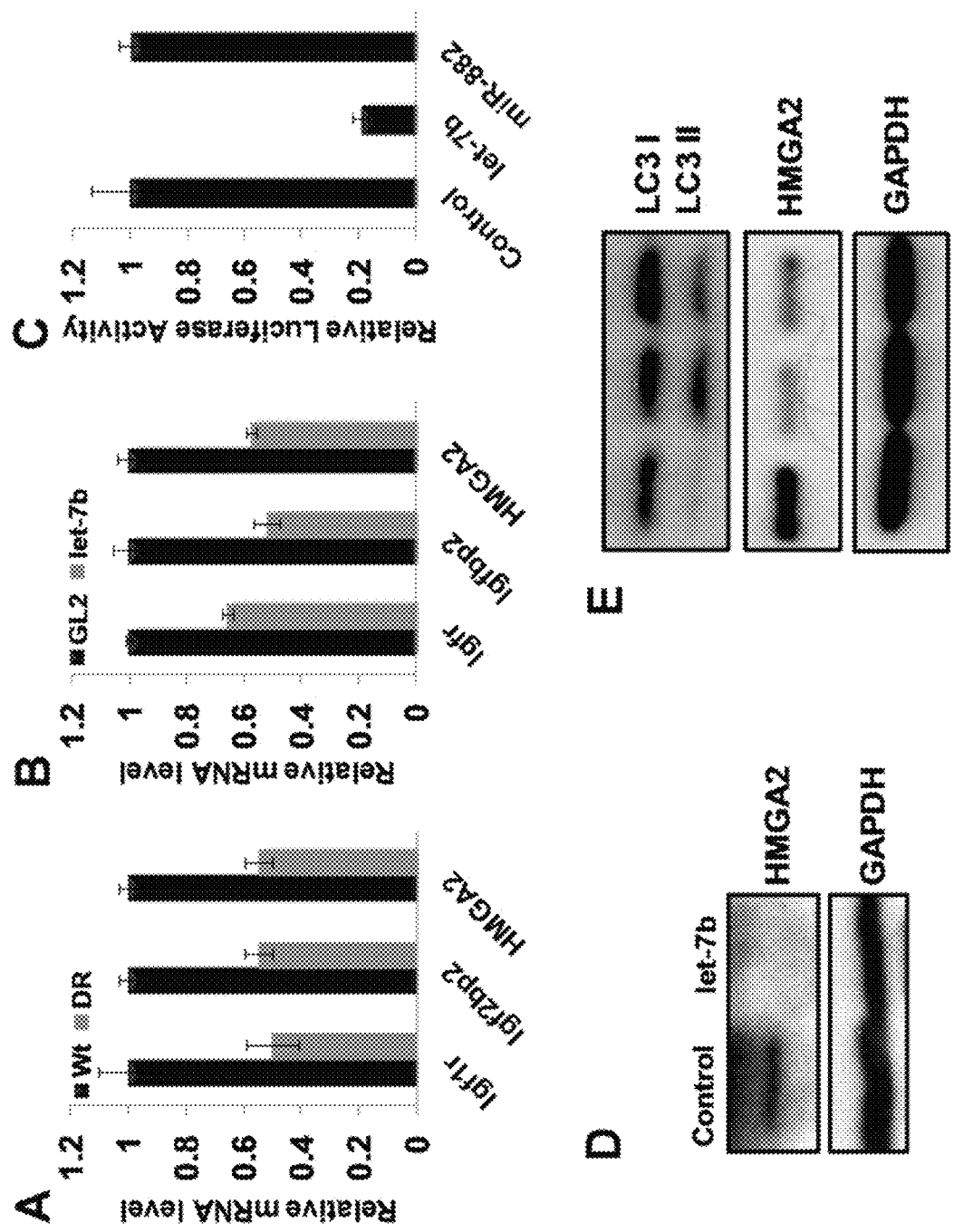
FIG. 7 A-E

FIG. 9 A-C

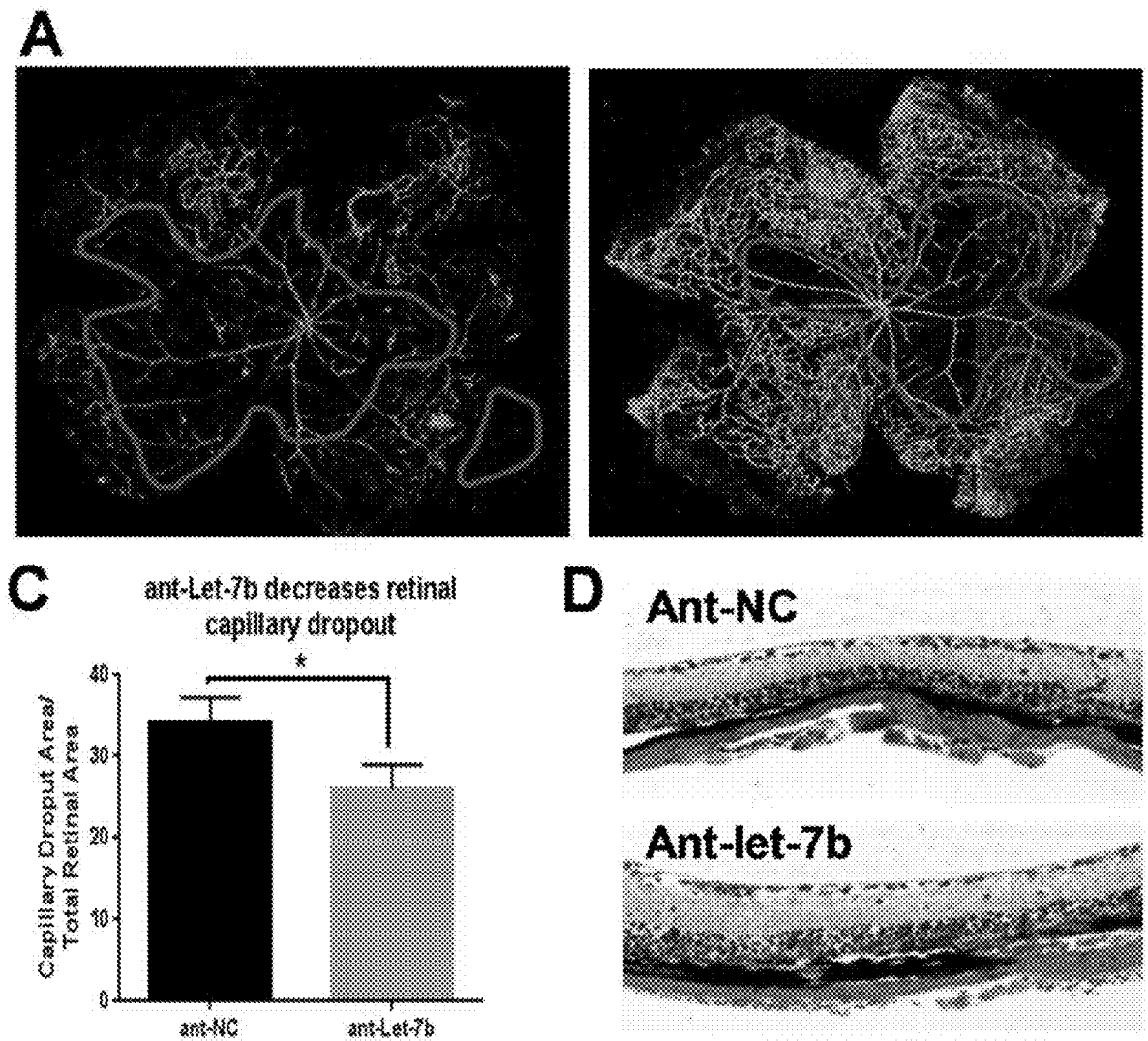
FIG 11 A-D

| RNA Sequence | 3' Overhang | Primer Name | SEQ. ID. NO. | Scale | 5' Mod | 3' Mod | Purification | Format |
|---|---|---|---|---|---|---|---|---|
| CGUACGCGGAAUACUUCGA | TT | GL2 | 5 | 80N | PHO | NONE | DSL | B |
| UCGAAGUAUUCCGCGUACG | TT | GL2 | 6 | 80N | PHO | NONE | DSL | B |
| UGAGGUAGUAGGUUGUGUGGUU | TT | let7b | 10 | 80N | PHO | NONE | DSL | B |
| AACCACACAACCUACUACCUCA | TT | let7b | 4 | 80N | PHO | NONE | DSL | B |

ORDERING CODES

5' MODIFICATION

| Modification | Code |
|---|---|
| Biotin | BIO |
| Fluorescein | FLO |
| Phosphate | PHO |
| None | # |

SEQUENCE CODES

| | |
|---|---|
| Adenine | A |
| Cytosine | C |
| Guanidine | G |
| Uracil | U |

PURIFICATION

| | |
|---|---|
| Desalted | DSL |
| HPLC | HPL |

FORMAT

| | |
|---|---|
| Single Stranded | # (default) |
| Duplex | B |

SCALES OF SYNTHESIS\*

| | |
|---|---|
| 20 nmoles | 20N |
| 80 nmoles | 80N |

3' Overhang

| | |
|---|---|
| | dTdT |

\* Amount of CPG at start of synthesis. Product yield will be less.

FIG. 12

SEQUENCE LISTING

<160> NUMBER OF SEQ ID NOS: 10

<210> SEQ ID NO 1
<211> LENGTH: 22
<212> TYPE: RNA
<213> ORGANISM: Homo sapiens

<400> SEQUENCE: 1
aaccacacaa ccuacuaccu ca                                              22

<210> SEQ ID NO 2
<211> LENGTH: 14
<212> TYPE: RNA
<213> ORGANISM: Homo sapiens

<400> SEQUENCE: 2
aaccacacaa ccua                                                       14

<210> SEQ ID NO 3

-continued

```
<211> LENGTH: 24
<212> TYPE: DNA
<213> ORGANISM: Homo sapiens

<400> SEQUENCE: 3
ugagguagua gguugugugg uutt                                              24

<210> SEQ ID NO 4
<211> LENGTH: 24
<212> TYPE: DNA
<213> ORGANISM: Homo sapiens

<400> SEQUENCE: 4
aaccacacaa ccuacuaccu catt                                              24

<210> SEQ ID NO 5
<211> LENGTH: 21
<212> TYPE: DNA
<213> ORGANISM: Homo sapiens

<400> SEQUENCE: 5
cguacgcgga auacuucgat t                                                 21

<210> SEQ ID NO 6
<211> LENGTH: 21
<212> TYPE: DNA
<213> ORGANISM: Homo sapiens

<400> SEQUENCE: 6
ucgaaguauu ccgcguacgt t                                                 21

<210> SEQ ID NO 7
<211> LENGTH: 22
<212> TYPE: RNA
<213> ORGANISM: Homo sapiens

<400> SEQUENCE: 7
ugagguagua gguugugugg uu                                                22

<210> SEQ ID NO 8
<211> LENGTH: 19
<212> TYPE: RNA
<213> ORGANISM: Homo sapiens

<400> SEQUENCE: 8
cguacgcgga auacuucga                                                    19

<210> SEQ ID NO 9
<211> LENGTH: 19
<212> TYPE: RNA
<213> ORGANISM: Homo sapiens

<400> SEQUENCE: 9
ucgaaguauu ccgcguacg                                                    19

<210> SEQ ID NO 10
<211> LENGTH: 24
<212> TYPE: DNA
<213> ORGANISM: Homo sapiens

<400> SEQUENCE: 10
ugagguagua gguugugugg uutt                                              24
```

COMPOSITIONS AND METHODS FOR TREATING DIABETIC RETINOPATHY

CROSS REFERENCE TO RELATED APPLICATIONS

This application is a national stage filing of International Application No. PCT/US2016/055812, filed Oct. 6, 2016, which claims priority pursuant to 35 U.S.C. § 119(e) to U.S. provisional patent application No. 62/237,883 filed on Oct. 6, 2015. The entire disclosures of the afore-mentioned patent applications are incorporated herein by reference.

STATEMENT REGARDING FEDERALLY SPONSORED RESEARCH OR DEVELOPMENT

This invention was made with government support under Grant No. EY022063 awarded by The National Institutes of Health. The government has certain rights in the invention.

BACKGROUND

Over 23 million U.S. residents have diabetes, and this number is predicted to double over the next thirty years. In 2002, direct medical expenditures on diabetes totaled $92 billion and indirect expenditures resulting from lost workdays and disability totaled $40 billion, roughly 18% of all U.S. health expenditures in 2002. Much of this disability results from diabetic retinopathy, which is found in nearly 100% of Type 1 and 60% of Type 2 diabetic patients within 20 years of diagnosis. The incidence of diabetic macular edema leading to vision loss is almost 30% after 20 years of disease in Type 1 and Type 2 patients. Proliferative retinopathy leaves as many as 24,000 patients blind each year due to ocular complications from this disease, making diabetic retinopathy the leading cause of blindness in all patients age 20-74 years old. Because the duration of diabetes is more predictive of diabetic retinopathy than mean blood glucose, diabetic retinopathy is of particular concern to Type 1 diabetic patients who often are diagnosed early in life and live decades as diabetic patients.

Chronic hyperglycemia leads to disruption of the vessels, making endothelial cells susceptible to diabetic conditions and causing elimination of (and dysfunction in) pericytes, which are vascular support cells that surround all capillaries in the retina. In turn, this results in microaneurysms, venous changes, retinal capillary loss, retinal ischemia, and ultimately blindness.

Diabetes profoundly impacts the microvasculature in nearly every tissue. Diabetic retinopathy results in retinal capillary dropout, vessel leakage, and pathological neovascularization, leading to severe and irreversible vision loss. Current surgical and pharmacologic treatments are only effective at managing complications of diabetic retinopathy, but do not prevent against or repair existing retinal damage. Laser photocoagulation is the current treatment standard for proliferative diabetic retinopathy, and operates on the principle of cauterizing hypoxic retinal tissue. While effective at stemming the progression of retinopathy, this procedure damages peripheral and night vision, often requires repeated treatments, and only prevents visual deterioration in half of cases. Anti-VEGF therapy has been increasingly used alone or in combination with laser therapy, with improvements in vision loss due to diabetic macular edema. However, anti-VEGF therapy requires frequent intra-vitreal injection and does not reverse the underlying pathology.

There is a long felt need in the art for compositions and methods useful for preventing and treating microvascular disease, in particular microvascular diseases due to diabetes. Similarly, there is a need for preventing and treating including retinopathy, many often due to underlying microvascular disease, in particular diabetic retinopathy. The present invention satisfies these needs.

SUMMARY OF THE INVENTION

MicroRNA (miRNA) inhibitors are particularly promising for addressing microvascular disease, in particular diabetic microvascular disease, because these are small molecules, easy to deliver, have a well established safety profile, and they are currently being evaluated in pre-clinical and clinical trials for several diseases.

It is disclosed herein that increased levels of miRNA let-7b are associated with various aspects of diabetic retinopathy. It is further disclosed herein that delivery of an inhibitor of miRNA let-7b into the eye improves retinal vasculature stability and prevents the loss of retinal blood vessels, which would otherwise lead to blindness. It is also disclosed herein that once delivered an inhibitor of miRNA let-7b localizes in the retinal tissue, with high expression in the retinal microvasculature. Therefore, the present invention encompasses the use of compositions and methods to inhibit microRNA let-7b activity, levels, and expression. In one aspect, the inhibitor of microRNA let-7b is an antagomir.

Based on the data disclosed herein, the present invention further encompasses compositions and methods for inhibiting other members of the let-7 family that, similar to let-7b miRNA, increase in expression along with let-7b miRNA. For example, let-7c-5p and let-7i-5p are also disclosed herein to be overexpressed. In one aspect, the expression increases in a microvasculature diseases. Therefore, the present invention provides compositions and method for inhibiting the harmful effects of increased levels or activity of miRNA let-7 family members wherein the increased levels or activity are associated with an injury, disease, or disorder, particularly an injury, disease, or disorder of the microvasculature. In one aspect, one inhibitor is used. In another aspect, more than one inhibitor is used. In another aspect, when more than one inhibitor is used, they can be directed against different members of the let-7 family of miRNAs.

In one embodiment, the present invention provides compositions and methods useful for preventing and treating retinopathy. In one aspect, the retinopathy is diabetic retinopathy. In one aspect, treatment methods of the present invention include administering a composition comprising at least one inhibitor of microRNA let-7b to a subject in need thereof. In one aspect, the inhibitor is a nucleic acid. In one aspect, the compositions and methods of the invention are useful for vasculature stabilization in the eye. In one aspect, the compositions and methods are useful to preserve retinal tissue. In one aspect, the invention is useful for reducing retinal capillary dropout. In one aspect, the invention is useful for diminishing microvascular leakage. In one aspect, the invention is useful for preventing or treating hyperproliferation of microvascular cells.

In one embodiment, a pharmaceutical composition of the invention comprises at least one inhibitor of a member of the let-7 miRNA family or other miRNA that demonstrates increased expression. In one aspect, the inhibitor inhibits miRNA let-7b. In one aspect, the inhibitor is an antagomir of miRNA let-7b.

In one embodiment, an inhibitor of the invention is administered into the eye. In one aspect, it is administered intravitreally. In one aspect, more than one inhibitor is administered as part of a combination therapy.

In one embodiment, the present invention is useful for preventing or treating microvasculature diseases and disorders where an increase in a let-7 miRNA is associated with an injury, disease, or disorder of the microvasculature. In one aspect, the disease or disorder is a retinal microvasculature disease. In one aspect, the retinal disease or disorder is degenerative. In one aspect, it is a degenerative retinopathy.

The present invention does not just encompass administering pharmaceutical compositions comprising an effective amount of an inhibitor of miRNA or an isolated nucleic acid encoding the inhibitor. The present invention further encompasses targeting cells that express the miRNA being targeted. In one aspect, the miRNA is let-7b.

In one embodiment, an miRNA let-7b inhibitor of the invention is a nucleic acid having the sequence "AACCACACAACCUACUACCUCA" (SEQ ID NO: 1), or a biologically active homolog or fragment thereof. In one aspect, the sequence is modified. In one aspect, the sequence is modified by being 2'-O-methylated at one or more nucleotides. In one aspect, each nucleotide is 2'-O-methylated. In one aspect, the nucleic acid is modified with a detectable label. In one aspect, the detectable label is a fluorescent label. In one aspect, the fluorescent label is Dy-547. In one aspect, the nucleic acid comprises a cholesterol molecule. In one aspect, the nucleic acid comprises a cholesterol molecule at the 3' end of the sequence. In one aspect, the cholesterol is linked through a hydroxyprolinol linkage. In one aspect, the nucleic acid comprises one or more phosphorothioate linkages. In one aspect, the sequence comprises multiple phosphorothioate modifications. In one aspect, there are 2, 3, 4, 5, 6, 7, 8, 9, or 10 phosphorothioate linkages. In one aspect, one or more nucleotides are 2'-O-methoxyethylated. In one aspect, the nucleic acid has multiple 2'-O-methoxyethylations. In one aspect, at least one nucleotide of the sequence is LNA modified. In one aspect, each nucleotide of the sequence is LNA modified. In one aspect, the antagomir has the sequence AACCACACAACCUA (SEQ ID NO:2). In one aspect, a nucleic acid having SEQ ID NO:2 is modified.

In one embodiment, a nucleic acid of the invention comprises two or more of the types of modifications described herein. For example, a nucleic acid of the invention may comprise two or more modifications of one or more nucleotides that are 2'-O-methylated, a detectable label, one or more phosphorothioate modifications, one or more nucleotides with an LNA modification, and a cholesterol, etc., including various combinations thereof. Various combinations are disclosed herein.

Inhibitors of the invention include, but are not limited to: Antagomir-let7b (ant-let7b), LNA-Chl antisense of let-7b, LNA antisense let-7b, MOE antisense let-7b, truncated ant-let7b, LNA-Chl antisense let-7b mini, LNA antisense let-7b mini, and MOE antisense let-7b mini. The modified nucleic acids are all related to SEQ ID NOs:1 and 2 and include various modifications as disclosed herein. See the descriptions of the various sequences and inhibitors in the Figures, Embodiments, and Examples. For example, Antagomir-let7b, also referred to as ant-let 7b and let-7b antagomir, comprises the detectable label DY547, 2'-O-methyl moieties at all nucleotides, five phosphorothioate modifications, and a 3' cholesterol modification of a nucleic acid having the sequence SEQ ID NO: 1. See the Embodiments and Examples sections for specifics regarding the modifications of the nucleic acid.

In one embodiment, the present invention provides compositions and methods for using a let-7b inhibitor that is an antagomir of let-7b. In one aspect, the antagomir comprises the sequence SEQ ID NO: 1, or a biologically active homolog or fragment thereof or at least one modification thereof. In one aspect, one or more nucleotides of the antagomir sequence are modified. In one aspect, one or more of the nucleotides is 2'-O-methylated. In one aspect, one or more phosphorothioate linkages are used. In one aspect, a cholesterol is added to the antagomir. In one aspect, the cholesterol is linked to the nucleic acid through a hydroxyprolinol linkage. In one aspect, there is LNA modification. In one aspect, one or more nucleotides is 2'-O-methoxyethylated.

Basic sequences of the invention, some of which are modified as disclosed herein for use as inhibitors, include:

1.
AACCACACAACCUACUACCUCA (SEQ ID NO: 1) and modifications thereof:

2.
                                          (SEQ ID NO: 2)
AACCACACAACCUA and modifications thereof 3.
                                          (SEQ ID NO: 3)
UGAGGUAGUAGGUUGUGUGGUU TT
let-7b first strand 4.
                                          (SEQ ID NO: 4)
AACCACACAACCUACUACCUCATT
let-7b complementary strand 5.
                                          (SEQ ID NO: 5)
CGUACGCGGAAUACUUCGATT
control miR first strand 6.
                                          (SEQ ID NO: 6)
UCGAAGUAUUCCGCGUACGTT
control miR complementary strand 7.
                                          (SEQ ID NO: 7)
UGAGGUAGUAGGUUGUGUGGUU
let-7b sequence; accession number MIMAT0001760

8.
                                          (SEQ ID NO: 8)
CGUACGCGGAAUACUUCGA 9.
                                          (SEQ ID NO: 9)
UCGAAGUAUUCCGCGUACG 10.
                                          (SEQ ID NO: 10)
UGAGGUAGUAGGUUGUGUGGUUTT

Inhibitors of the invention include, but are not limited to, Antagomir let-7b (ant-let7b), LNA-Chl antisense of let-7b, LNA antisense let-7b, MOE antisense let-7b, truncated ant-let7b, LNA-Chl antisense let-7b mini, LNA antisense let-7b mini, and MOE antisense let-7b mini. These nucleic acids are all related to SEQ ID NOs:1 or 2 and some include various modifications as disclosed herein. See the Embodiments and Examples sections for specifics regarding the modifications of these nucleic acids.

In one embodiment, the present invention provides an oligonucleotide directed against miRNA let-7b.

In one embodiment, a nucleic acid of the invention binds to miRNA let-7b.

In one embodiment, inhibition of miRNA let-7b protects the diabetic retina. In one aspect, inhibition of miRNA Let-7b decreases retinal capillary dropout.

In one embodiment, the present invention provides compositions and methods for treating diabetic retinopathy comprising administering to a subject in need thereof a pharmaceutical composition comprising an effective amount of an inhibitor of miRNA let-7b.

In one embodiment, intravitreally injected Dy-547 conjugated let-7b inhibitor localizes uniformly in the retinal vasculature.

In one aspect, the inhibitor is the antagomir Dy547-mA (*)mA(*)mCmCmAmCmAmCmAmAmCmCmUmAmC-mUmAmCmCmU(*)m C(*)mA (*)(3'-Chl), referred to as Antagomir-let-7b (ant-let-7b) herein. In one aspect, the nucleic acid is not labeled. The present invention further encompasses the use of other antagomirs of miRNA let-7b, including modifications of the antagomir described above. Inhibitors of the invention can include a detectable label. In one aspect, the detectable label is a fluorescent label. In one aspect, the label is Dy547. Methods for preparing nucleic acids of the invention are described herein or are known in the art (see Chen et al., 2012, Cell Reports, Vol. 2, pp. 1684-1696).

One of ordinary skill in the art will appreciate that the dosage of the nucleic acid administered can vary and that the number of times that the composition comprising the nucleic acid administered can be varied, depending on such things as the severity of the retinopathy, the age, sex, and health of the subject, etc. The inhibitor can also be administered in conjunction with other therapeutic agents or antibiotics or cells.

One of ordinary skill in the art will understand that an miRNA let-7b inhibitor of the invention, or other inhibitor of the invention, is also useful for treating other diseases, conditions or disorders of aberrant let-7b or other let-7 family member expression, activity, or levels or where inhibition of let-7b expression, activity, or levels would be beneficial.

In one embodiment, the nucleic acids of the invention are double stranded.

The compositions and methods of the present invention provide a vast technological improvement over prior methods to prevent or treat diabetic retinopathy.

Various aspects and embodiments of the invention are described in further detail below.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 4A-B: Autophagy is induced in the retina of diabetic retinopathy. (A; comprising 6 panels) LC3 is highly expressed in the superficial retinal vasculature and RGCs of Akimba retina. Retinas from WT and Akimba mice were stained with lectin (green) and PDGFRβ (red) to visualize vessels and perivascular cells. LC3 was higher in the retinal vasculature/RGCs of the superficial plane of Akimba mice. Scale bar=50 µm. (B; comprising 6 panels) P62 is decreased in the superficial retinal vasculature of Akimba mice. WT and Akimba whole mount retinas were stained with lectin (green for vasculature), PDGFRβ (red for perivascular cells), and p62 (orange). The superficial vasculature plane of 7 Akimba retinas showed decreased p62 expression in the RGC/interstitial space and retinal vasculature (dashed-circled) when compared to age-matched WT retina. P62 is expected to decrease with induction of autophagy. DAPI: blue. Scale bar=100 µm.

FIG. 5A-C: LC3 is increased in the areas of DR retinas where let-7b is upregulated. (A; comprising 6 panels) LC3 is increased in Akimba retinal section. Antigen-retrieval immunohistochemistry was performed on frozen retinal sections of wildtype (WT) and Akimba mice (n=4) to determine LC3 expression (red). Unlike WT retina, LC3 expression is high in the retinal ganglion cell (RGC) and inner plexiform layer (IPL) of Akimba retina (yellow box inset). The white asterisk indicates the RGC layer, while the arrow heads mark the inner segment-outer segment. Quantification of LC3 using image analysis demonstrates that LC3 is significantly (*$p<0.05$) higher in the IPL (B) and the entire retina (C). Scale bar=100 µm.

FIG. 6A-C: let-7b induces autophagy in human retinal pericytes and mouse retina. let-7b induces autophagy in human retinal pericytes and in mouse retina. (A; comprising 4 panels) Let-7b induces autophagy in human retinal pericytes as marked by transfected GFP-LC3b puncta (green). (B) Western blot demonstrates let-7b transfection induces endogenous autophagy markers in human retinal pericytes, while (C) intravitreal injection of let-7b induces autophagy in the retina of WT mice.

FIG. 7A-E: let-7b induces autophagy by downregulating the genes upstream of mTORC1 and FoxO3A pathway. (A, B) Relative mRNA levels of Igfr, Igfbp2, and HMGA2 are downregulated in Akimba retinas and let-7b transfected human retinal pericytes (HRPs). (C) let-7b (not a non-specific miR-882) co-transfected with PRL-HMGA2 3'UTR luciferase construct suppresses luciferase activity in HRPs. (D) HMGA2 is downregulated in let-7b transfected HRPs. (E) Transfection of HMGA2 siRNA into human retinal pericytes (HRPs) increases LC3-II.

FIG. 11A-D: Inhibition of let-7b protects the diabetic retina. Intravitreal injection of let-7b antagomiRs (ant-let7b) into male Akimba mice decreases retinal capillary dropout. Six-week old male mice Akimba mice (n=6) were injected with let-7b antagomiR (ant-let-7b) in the one eye and negative control antagomiR (ant-NC) in the contralateral eye. At 10 weeks, ant-let-7b injected retinas (B) protected capillary dropout (circled in when red) compared to ant-NC-injected retinas (A). (C) Injection of ant-let-7b significantly reduces ($*p<0.05$) the ratio of capillary dropout to total retinal area by approximately 24% relative to the control injection. (D) Injection of let-7b inhibitor protects the retinal thickness and cellularity as compared to control inhibitor.

FIG. 12. Some AntagomiR sequences and sequence information

DETAILED DESCRIPTION

Abbreviations and Acronyms

Figure 1:
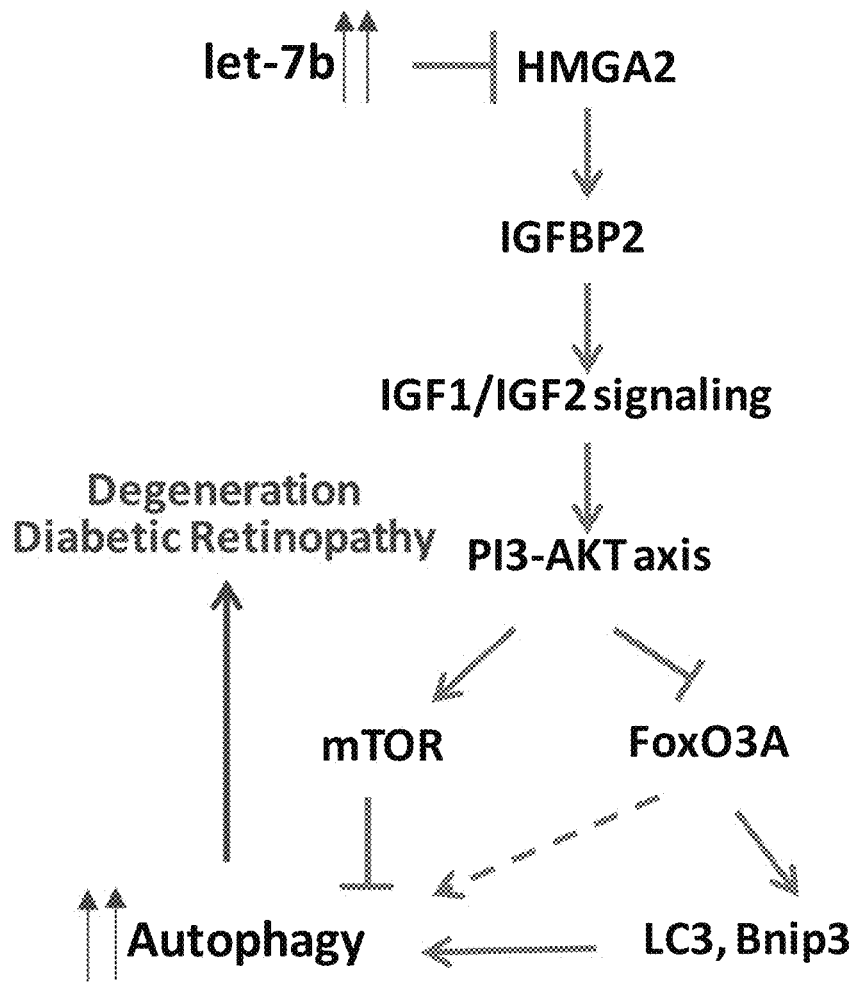
FIG. 1: Schematic of signaling and sequences of events in Diabetic Retinopathy and role of let-7b. let-7b promotes autophagy either by repressing mTOR activity, or inducing FoxO3A transcription and activity through PI3-AKT signaling cascade by downregulating HMGA2. FoxO3A induces autophagy by increasing LC3 & Bnip3. Dysregulation of let-7b/HMGA2 axis impaired autophagy that leads to degeneration of retinal vasculature and DR.

ASC—adipose derived stem cell
chl—cholesterol
DR—diabetic retinopathy
FISH—fluorescence in situ hybridization
HRP—human retinal pericyte
IPL—inner plexiform layer
l—when in a nucleic sequence indicates an LNA modification
LNA—locked nucleic acid
m—2'-O-methyl moiety/modification
me—indicates 2'-O-methoxyethyl modification
miR—micro-RNA (also referred to as miRNA)
miRNA—micro-RNA (also referred to as miR)
NC—negative control
NPDR—non-proliferative diabetic retinopathy
PDGF—platelet-derived growth factor
PDGFR—PDGF receptor
PDR—proliferative diabetic retinopathy
RGC—retinal ganglion cell
siRNA—small interfering RNA
VEGF—vascular endothelial growth factor
WT—wild type
*—when in a nucleic acid sequence indicates a phosphorothioate

Definitions

In describing and claiming the invention, the following terminology will be used in accordance with the definitions set forth below.

In describing and claiming the invention, the following terminology will be used in accordance with the definitions set forth below.

The articles "a" and "an" are used herein to refer to one or to more than one (i.e., to at least one) of the grammatical object of the article. By way of example, "an element" means one element or more than one element.

The term "about," as used herein, means approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 10%. In one aspect, the term "about" means plus or minus 10% of the numerical value of the number with which it is being used. Therefore, about 50% means in the range of 45%-55%. Numerical ranges recited herein by endpoints include all numbers and fractions subsumed within that range (e.g. 1 to 5 includes 1, 1.5, 2, 2.75, 3, 3.90, 4, and 5). It is also to be understood that all numbers and fractions thereof are presumed to be modified by the term "about."

The terms "additional therapeutically active compound" or "additional therapeutic agent", as used in the context of the present invention, refers to the use or administration of a compound for an additional therapeutic use for a particular injury, disease, or disorder being treated. Such a compound, for example, could include one being used to treat an unrelated disease or disorder, or a disease or disorder which may not be responsive to the primary treatment for the injury, disease or disorder being treated. Disease and disorders being treated by the additional therapeutically active agent include, for example, hypertension and diabetes. The additional compounds may also be used to treat symptoms associated with the injury, disease, or disorder, including, but not limited to, pain and inflammation.

"Adipose-derived stem cells", also referred to as "adipose-derived stromal cells" herein, refer to cells that originate from adipose tissue. By "adipose" is meant any fat tissue. The adipose tissue may be brown or white adipose tissue, derived from subcutaneous, omental/visceral, mammary, gonadal, or other adipose tissue site. Preferably, the adipose is subcutaneous white adipose tissue. Such cells may comprise a primary cell culture or an immortalized cell line. The adipose tissue may be from any organism having fat tissue. Preferably, the adipose tissue is mammalian, more preferably, the adipose tissue is human. A convenient source of adipose tissue is from liposuction surgery, however, the source of adipose tissue or the method of isolation of adipose tissue is not critical to the invention.

As used herein, the term "adjuvant" refers to a substance that elicits an enhanced immune response when used in combination with a specific antigen.

As use herein, the terms "administration of" and or "administering" a compound should be understood to mean providing a compound of the invention or a prodrug of a compound of the invention to a subject in need of treatment.

The term "adult" as used herein, is meant to refer to any non-embryonic or non-juvenile subject. For example the term "adult adipose tissue stem cell," refers to an adipose stem cell, other than that obtained from an embryo or juvenile subject.

As used herein, an "agent" is meant to include something being contacted with a cell population to elicit an effect, such as a drug, a protein, a peptide. An "additional therapeutic agent" refers to a drug or other compound used to treat an illness and can include, for example, an antibiotic or a chemotherapeutic agent.

As used herein, an "agonist" is a composition of matter which, when administered to a mammal such as a human, enhances or extends a biological activity attributable to the level or presence of a target compound or molecule of interest in the mammal.

An "antagonist" is a composition of matter which when administered to a mammal such as a human, inhibits a biological activity attributable to the level or presence of a compound or molecule of interest in the mammal.

As used herein, "alleviating a disease or disorder symptom," means reducing the severity of the symptom or the frequency with which such a symptom is experienced by a patient, or both.

As used herein, an "analog" of a chemical compound is a compound that, by way of example, resembles another in structure but is not necessarily an isomer (e.g., 5-fluorouracil is an analog of thymine).

As used herein, amino acids are represented by the full name thereof, by the three letter code corresponding thereto, or by the one-letter code corresponding thereto, as indicated in the following table:

| Full Name | Three-Letter Code | One-Letter Code |
|---|---|---|
| Aspartic Acid | Asp | D |
| Glutamic Acid | Glu | E |
| Lysine | Lys | K |
| Arginine | Arg | R |
| Histidine | His | H |
| Tyrosine | Tyr | Y |
| Cysteine | Cys | C |
| Asparagine | Asn | N |
| Glutamine | Gln | Q |
| Serine | Ser | S |
| Threonine | Thr | T |
| Glycine | Gly | G |
| Alanine | Ala | A |
| Valine | Val | V |
| Leucine | Leu | L |
| Isoleucine | Ile | I |
| Methionine | Met | M |
| Proline | Pro | P |
| Phenylalanine | Phe | F |
| Tryptophan | Trp | W |

The expression "amino acid" as used herein is meant to include both natural and synthetic amino acids, and both D and L amino acids. "Standard amino acid" means any of the twenty standard L-amino acids commonly found in naturally occurring peptides. "Nonstandard amino acid residue" means any amino acid, other than the standard amino acids, regardless of whether it is prepared synthetically or derived from a natural source. As used herein, "synthetic amino acid" also encompasses chemically modified amino acids, including but not limited to salts, amino acid derivatives (such as amides), and substitutions. Amino acids contained within the peptides of the present invention, and particularly at the carboxy- or amino-terminus, can be modified by methylation, amidation, acetylation or substitution with other chemical groups which can change the peptide's circulating half-life without adversely affecting their activity. Additionally, a disulfide linkage may be present or absent in the peptides of the invention.

The term "amino acid" is used interchangeably with "amino acid residue," and may refer to a free amino acid and to an amino acid residue of a peptide. It will be apparent from the context in which the term is used whether it refers to a free amino acid or a residue of a peptide.

Amino acids have the following general structure:

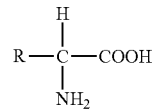

Amino acids may be classified into seven groups on the basis of the side chain R: (1) aliphatic side chains, (2) side chains containing a hydroxylic (OH) group, (3) side chains containing sulfur atoms, (4) side chains containing an acidic or amide group, (5) side chains containing a basic group, (6) side chains containing an aromatic ring, and (7) proline, an imino acid in which the side chain is fused to the amino group.

The nomenclature used to describe the peptide compounds of the present invention follows the conventional practice wherein the amino group is presented to the left and the carboxy group to the right of each amino acid residue. In the formulae representing selected specific embodiments of the present invention, the amino- and carboxy-terminal groups, although not specifically shown, will be understood to be in the form they would assume at physiologic pH values, unless otherwise specified.

The term "basic" or "positively charged" amino acid as used herein, refers to amino acids in which the R groups have a net positive charge at pH 7.0, and include, but are not limited to, the standard amino acids lysine, arginine, and histidine.

The term "antagomir" refers to a small RNA or DNA (or chimeric) molecule to antagonize endogenous small RNA regulators like microRNA (miRNA). These antagonists bear complementary nucleotide sequences for the most part, which means that antagomirs should hybridize to the mature microRNA (miRNA). They prevent other molecules from binding to a desired site on an mRNA molecule and are used to silence endogenous microRNA (miR). Antagomirs are therefore designed to block biological activity of these post-transcriptional molecular switches. Like the preferred target ligands (microRNA, miRNA), antagomirs have to cross membranes to enter a cell. Antagomirs also known as anti-miRs or blockmirs.

MicroRNAs are generally about 16-25 nucleotides in length. In one aspect, miRNAs are RNA molecules of 22 nucleotides or less in length. These molecules have been found to be highly involved in the pathology of several types of cancer. Although the miRNA molecules are generally found to be stable when associated with blood serum and its components after EDTA treatment, introduction of locked nucleic acids (LNAs) to the miRNAs via PCR further increases stability of the miRNAs. LNAs are a class of nucleic acid analogues in which the ribose ring is "locked" by a methylene bridge connecting the 2'-O atom and the 4'-C atom of the ribose ring, which increases the molecule's affinity for other molecules. miRNAs are species of small non-coding single-stranded regulatory RNAs that interact with the 3'-untranslated region (3'-UTR) of target mRNA molecules through partial sequence homology. They participate in regulatory networks as controlling elements that direct comprehensive gene expression. Bioinformatics analysis has predicted that a single miRNA can regulate hundreds of target genes, contributing to the combinational and subtle regulation of numerous genetic pathways.

The term "antibody," as used herein, refers to an immunoglobulin molecule which is able to specifically bind to a specific epitope on an antigen. Antibodies can be intact immunoglobulins derived from natural sources or from recombinant sources and can be immunoreactive portions of intact immunoglobulins. Antibodies are typically tetramers of immunoglobulin molecules. The antibodies in the present invention may exist in a variety of forms including, for example, polyclonal antibodies, monoclonal antibodies, Fv, Fab and $F(ab)_2$, as well as single chain antibodies and humanized antibodies.

As used herein, the term "antisense oligonucleotide" or antisense nucleic acid means a nucleic acid polymer, at least a portion of which is complementary to a nucleic acid which is present in a normal cell or in an affected cell. "Antisense" refers particularly to the nucleic acid sequence of the non-coding strand of a double stranded DNA molecule encoding a protein, or to a sequence which is substantially homologous to the non-coding strand. As defined herein, an antisense sequence is complementary to the sequence of a double stranded DNA molecule encoding a protein. It is not necessary that the antisense sequence be complementary solely to the coding portion of the coding strand of the DNA molecule. The antisense sequence may be complementary to regulatory sequences specified on the coding strand of a DNA molecule encoding a protein, which regulatory sequences control expression of the coding sequences. The antisense oligonucleotides of the invention include, but are not limited to, phosphorothioate oligonucleotides and other modifications of oligonucleotides.

An "aptamer" is a compound that is selected in vitro to bind preferentially to another compound (for example, the identified proteins herein). Often, aptamers are nucleic acids or peptides because random sequences can be readily generated from nucleotides or amino acids (both naturally occurring or synthetically made) in large numbers but of course they need not be limited to these.

The term "autologous", as used herein, refers to something that occurs naturally and normally in a certain type of tissue or in a specific structure of the body.

In transplantation, it refers to a graft in which the donor and recipient areas are in the same individual, or to blood that the donor has previously donated and then receives back, usually during surgery.

The term "basal medium", as used herein, refers to a minimum essential type of medium, such as Dulbecco's Modified Eagle's Medium, Ham's F12, Eagle's Medium, RPMI, AR8, etc., to which other ingredients may be added. The term does not exclude media which have been prepared or are intended for specific uses, but which upon modification can be used for other cell types, etc.

The term "blastema", as used herein, encompasses inter alia, the primordial cellular mass from which an organ, tissue or part is formed as well as a cluster of cells competent to initiate and/or facilitate the regeneration of a damaged or ablated structure.

The term "biocompatible," as used herein, refers to a material that does not elicit a substantial detrimental response in the host.

The term "biodegradable," as used herein, means capable of being biologically decomposed. A biodegradable material differs from a non-biodegradable material in that a biodegradable material can be biologically decomposed into units which may be either removed from the biological system and/or chemically incorporated into the biological system.

As used herein, the term "biologically active fragments" or "bioactive fragment" of the polypeptides encompasses natural or synthetic portions of the full-length protein that are capable of specific binding to their natural ligand or of performing the function of the protein.

The term "biological sample," as used herein, refers to samples obtained from a subject, including, but not limited to, skin, hair, tissue, blood, plasma, cells, sweat and urine.

The term "bioresorbable," as used herein, refers to the ability of a material to be resorbed in vivo. "Full" resorption means that no significant extracellular fragments remain. The resorption process involves elimination of the original implant materials through the action of body fluids, enzymes, or cells. Resorbed calcium carbonate may, for example, be redeposited as bone mineral, or by being otherwise re-utilized within the body, or excreted. "Strongly bioresorbable," as the term is used herein, means that at least 80% of the total mass of material implanted is resorbed within one year.

The terms "cell" and "cell line," as used herein, may be used interchangeably. All of these terms also include their progeny, which are any and all subsequent generations. It is understood that all progeny may not be identical due to deliberate or inadvertent mutations.

The terms "cell culture" and "culture," as used herein, refer to the maintenance of cells in an artificial, in vitro environment. It is to be understood, however, that the term "cell culture" is a generic term and may be used to encompass the cultivation not only of individual cells, but also of tissues, organs, organ systems or whole organisms, for which the terms "tissue culture," "organ culture," "organ system culture" or "organotypic culture" may occasionally be used interchangeably with the term "cell culture."

The phrases "cell culture medium," "culture medium" (plural "media" in each case) and "medium formulation" refer to a nutritive solution for cultivating cells and may be used interchangeably.

A "compound," as used herein, refers to any type of substance or agent that is commonly considered a drug, or a candidate for use as a drug, combinations, and mixtures of the above, as well as polypeptides and antibodies of the invention.

A "conditioned medium" is one prepared by culturing a first population of cells or tissue in a medium, and then harvesting the medium. The conditioned medium (along with anything secreted into the medium by the cells) may then be used to support the growth or differentiation of a second population of cells.

A "control" cell, tissue, sample, or subject is a cell, tissue, sample, or subject of the same type as a test cell, tissue, sample, or subject. The control may, for example, be examined at precisely or nearly the same time the test cell, tissue, sample, or subject is examined. The control may also, for example, be examined at a time distant from the time at which the test cell, tissue, sample, or subject is examined, and the results of the examination of the control may be recorded so that the recorded results may be compared with results obtained by examination of a test cell, tissue, sample, or subject. The control may also be obtained from another source or similar source other than the test group or a test subject, where the test sample is obtained from a subject suspected of having a disease or disorder for which the test is being performed.

A "test" cell, tissue, sample, or subject is one being examined or treated.

A "pathoindicative" cell, tissue, or sample is one which, when present, is an indication that the animal in which the cell, tissue, or sample is located (or from which the tissue was obtained) is afflicted with a disease or disorder. By way of example, the presence of one or more breast cells in a lung tissue of an animal is an indication that the animal is afflicted with metastatic breast cancer.

A tissue "normally comprises" a cell if one or more of the cell are present in the tissue in an animal not afflicted with a disease or disorder.

"Cytokine," as used herein, refers to intercellular signaling molecules, the best known of which are involved in the regulation of mammalian somatic cells. A number of families of cytokines, both growth promoting and growth inhibitory in their effects, have been characterized including, for example, interleukins, interferons, and transforming growth factors. A number of other cytokines are known to those of skill in the art. The sources, characteristics, targets and effector activities of these cytokines have been described.

The term "delivery vehicle" refers to any kind of device or material which can be used to deliver cells in vivo or can be added to a composition comprising cells administered to an animal. This includes, but is not limited to, implantable devices, aggregates of cells, matrix materials, gels, etc.

As used herein, a "derivative" of a compound refers to a chemical compound that may be produced from another compound of similar structure in one or more steps, as in replacement of H by an alkyl, acyl, or amino group.

The use of the word "detect" and its grammatical variants is meant to refer to measurement of the species without quantification, whereas use of the word "determine" or "measure" with their grammatical variants are meant to refer to measurement of the species with quantification. The terms "detect" and "identify" are used interchangeably herein.

A "disease" is a state of health of an animal wherein the animal cannot maintain homeostasis, and wherein if the disease is not ameliorated then the animal's health continues to deteriorate.

In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

As used herein, an "effective amount" means an amount sufficient to produce a selected effect. A "therapeutically effective amount" means an effective amount of an agent being used in treating or preventing a disease or disorder. As used herein, an "essentially pure" preparation of a particular protein or peptide is a preparation wherein at least about 95%, and preferably at least about 99%, by weight, of the protein or peptide in the preparation is the particular protein or peptide.

The term "feeder cells" as used herein refers to cells of one type that are co-cultured with cells of a second type, to provide an environment in which the cells of the second type can be maintained, and perhaps proliferate. The feeder cells can be from a different species than the cells they are supporting. Feeder cells can be non-lethally irradiated or treated to prevent their proliferation prior to being co-cultured to ensure to that they do not proliferate and mingle with the cells which they are feeding. The terms, "feeder cells", "feeders," and "feeder layers" are used interchangeably herein.

As used herein, a "functional" molecule is a molecule in a form in which it exhibits a property or activity by which it is characterized.

A "fragment" or "segment" is a portion of an amino acid sequence, comprising at least one amino acid, or a portion of a nucleic acid sequence comprising at least one nucleotide. The terms "fragment" and "segment" are used interchangeably herein.

As used herein, the term "fragment," as applied to a protein or peptide, can ordinarily be at least about 3-15 amino acids in length, at least about 15-25 amino acids, at least about 25-50 amino acids in length, at least about 50-75 amino acids in length, at least about 75-100 amino acids in length, and greater than 100 amino acids in length.

As used herein, the term "fragment" as applied to a nucleic acid, may ordinarily be at least about 20 nucleotides in length, typically, at least about 50 nucleotides, more typically, from about 50 to about 100 nucleotides, preferably, at least about 100 to about 200 nucleotides, even more preferably, at least about 200 nucleotides to about 300 nucleotides, yet even more preferably, at least about 300 to about 350, even more preferably, at least about 350 nucleotides to about 500 nucleotides, yet even more preferably, at least about 500 to about 600, even more preferably, at least about 600 nucleotides to about 620 nucleotides, yet even more preferably, at least about 620 to about 650, and most preferably, the nucleic acid fragment will be greater than about 650 nucleotides in length. In the case of a shorter sequence such as SEQ ID NO: 1, fragments are shorter.

As used herein, a "functional" biological molecule is a biological molecule in a form in which it exhibits a property by which it is characterized. A functional enzyme, for example, is one which exhibits the characteristic catalytic activity by which the enzyme is characterized.

"Graft" refers to any free (unattached) cell, tissue, or organ for transplantation.

"Allograft" or "allogeneic" refers to a transplanted cell, tissue, or organ derived from a different animal of the same species.

"Xenograft" or "xenogeneic" refers to a transplanted cell, tissue, or organ derived from an animal of a different species.

The term "growth factor" as used herein means a bioactive molecule that promotes the proliferation of a cell or tissue. Growth factors useful in the present invention include, but are not limited to, transforming growth factor-alpha (TGF-α), transforming growth factor-beta (TGF-β), platelet-derived growth factors including the AA, AB and BB isoforms (PDGF), fibroblast growth factors (FGF), including FGF acidic isoforms 1 and 2, FGF basic form 2, and FGF 4, 8, 9 and 10, nerve growth factors (NGF) including NGF 2.5s, NGF 7.0s and beta NGF and neurotrophins, brain derived neurotrophic factor, cartilage derived factor, bone growth factors (BGF), basic fibroblast growth factor, insulin-like growth factor (IGF), vascular endothelial growth factor (VEGF), EG-VEGF, VEGF-related protein, Bv8, VEGF-E, granulocyte colony stimulating factor (G-CSF), insulin like growth factor (IGF) I and II, hepatocyte growth factor, glial neurotrophic growth factor, stem cell factor (SCF), keratinocyte growth factor (KGF), skeletal growth factor, bone matrix derived growth factors, and bone derived growth factors and mixtures thereof. Some growth factors may also promote differentiation of a cell or tissue. TGF, for example, may promote growth and/or differentiation of a cell or tissue. Note that many factors are pleiotropic in their activity and the activity can vary depending on things such as the cell type being contacted, the state of proliferation or differentiation of the cell, etc.

"Homologous" as used herein, refers to the subunit sequence similarity between two polymeric molecules, e.g., between two nucleic acid molecules, e.g., two DNA molecules or two RNA molecules, or between two polypeptide molecules. When a subunit position in both of the two molecules is occupied by the same monomeric subunit, e.g., if a position in each of two DNA molecules is occupied by adenine, then they are homologous at that position. The homology between two sequences is a direct function of the number of matching or homologous positions, e.g., if half (e.g., five positions in a polymer ten subunits in length) of the positions in two compound sequences are homologous then the two sequences are 50% homologous, if 90% of the positions, e.g., 9 of 10, are matched or homologous, the two sequences share 90% homology. By way of example, the DNA sequences 3'ATTGCC5' and 3'TATGGC share 50% homology.

As used herein, "homology" is used synonymously with "identity."

The determination of percent identity between two nucleotide or amino acid sequences can be accomplished using a mathematical algorithm. For example, a mathematical algorithm useful for comparing two sequences is the algorithm of Karlin and Altschul (1990, Proc. Natl. Acad. Sci. USA 87:2264-2268), modified as in Karlin and Altschul (1993, Proc. Natl. Acad. Sci. USA 90:5873-5877). This algorithm is incorporated into the NBLAST and XBLAST programs of Altschul, et al. (1990, J. Mol. Biol. 215:403-410), and can be accessed, for example at the National Center for Biotechnology Information (NCBI) world wide web site. BLAST nucleotide searches can be performed with the NBLAST program (designated "blastn" at the NCBI web site), using the following parameters: gap penalty=5; gap extension penalty=2; mismatch penalty=3; match reward=1; expectation value 10.0; and word size=11 to obtain nucleotide sequences homologous to a nucleic acid described herein. BLAST protein searches can be performed with the XBLAST program (designated "blastn" at the NCBI web site) or the NCBI "blastp" program, using the following parameters: expectation value 10.0, BLOSUM62 scoring matrix to obtain amino acid sequences homologous to a protein molecule described herein. To obtain gapped alignments for comparison purposes, Gapped BLAST can be utilized as described in Altschul et al. (1997, Nucleic Acids Res. 25:3389-3402). Alternatively, PSI-Blast or PHI-Blast can be used to perform an iterated search which detects distant relationships between molecules (Id.) and relationships between molecules which share a common pattern. When utilizing BLAST, Gapped BLAST, PSI-Blast, and PHI-Blast programs, the default parameters of the respective programs (e.g., XBLAST and NBLAST) can be used.

The percent identity between two sequences can be determined using techniques similar to those described above, with or without allowing gaps. In calculating percent identity, typically exact matches are counted.

The term "improved blood flow," as used herein, refers to increased blood flow in a subject being treated according to the methods of the invention compared with the flow in a subject with an otherwise identical injury or condition not being treated according to the methods of the invention. Improved flow is determined by methods such as those described herein and can include less stasis, less sludging, or a combination of both, in the subject being treated compared with the untreated subject.

The term "ingredient" refers to any compound, whether of chemical or biological origin, that can be used in cell culture media to maintain or promote the proliferation, survival, or differentiation of cells. The terms "component," "nutrient", "supplement", and ingredient can be used interchangeably and are all meant to refer to such compounds. Typical non-limiting ingredients that are used in cell culture media include amino acids, salts, metals, sugars, lipids, nucleic acids, hormones, vitamins, fatty acids, proteins and the like. Other ingredients that promote or maintain cultivation of cells ex vivo can be selected by those of skill in the art, in accordance with the particular need.

The term "inhibit," as used herein, means to suppress or block an activity or function such that it is lower relative to a control value. The inhibition can be via direct or indirect mechanisms. In one aspect, the activity is suppressed or blocked by at least 10% compared to a control value, more preferably by at least 25%, and even more preferably by at least 50%.

The term "inhibitor" as used herein, refers to any compound or agent, the application of which results in the inhibition of a process or function of interest, including, but not limited to, expression, levels, and activity. Inhibition can be inferred if there is a reduction in the activity or function of interest.

The term "inhibitor of miRNA let-7b" refers to a compound or agent that inhibits the expression, levels, or activity of let-7b microRNA.

The term "inhibit a protein," as used herein, refers to any method or technique which inhibits protein synthesis, levels, activity, or function, as well as methods of inhibiting the induction or stimulation of synthesis, levels, activity, or function of the protein of interest. The term also refers to any metabolic or regulatory pathway which can regulate the synthesis, levels, activity, or function of the protein of interest. The term includes binding with other molecules and complex formation. Therefore, the term "protein inhibitor" refers to any agent or compound, the application of which results in the inhibition of protein function or protein pathway function. However, the term does not imply that each and every one of these functions must be inhibited at the same time.

As used herein "injecting or applying" includes administration of a compound or cells of the invention by any number of routes and means including, but not limited to, intravitreal, topical, oral, buccal, intravenous, intramuscular, intra arterial, intramedullary, intrathecal, intraventricular, transdermal, subcutaneous, intraperitoneal, intranasal, enteral, topical, sublingual, vaginal, ophthalmic, pulmonary, or rectal means.

The term "injury" refers to any physical damage to the body caused by violence, accident, trauma, or fracture, etc., as well as damage by surgery.

As used herein, an "instructional material" includes a publication, a recording, a diagram, or any other medium of expression which can be used to communicate the usefulness of the peptide of the invention in the kit for effecting alleviation of the various diseases or disorders recited herein. Optionally, or alternately, the instructional material may describe one or more methods of alleviating the diseases or disorders in a cell or a tissue of a mammal. The instructional material of the kit of the invention may, for example, be affixed to a container which contains the identified compound invention or be shipped together with a container which contains the identified compound. Alternatively, the instructional material may be shipped separately from the container with the intention that the instructional material and the compound be used cooperatively by the recipient.

Used interchangeably herein are the terms: 1) "isolate" and "select"; and 2) "detect" and "identify".

The term "isolated," when used in reference to cells, refers to a single cell of interest, or population of cells of interest, at least partially isolated from other cell types or other cellular material with which it naturally occurs in the tissue of origin (e.g., adipose tissue). A sample of stem cells is "substantially pure" when it is at least 60%, or at least 75%, or at least 90%, and, in certain cases, at least 99% free of cells other than cells of interest. Purity can be measured by any appropriate method, for example, by fluorescence-activated cell sorting (FACS), or other assays which distinguish cell types.

An "isolated nucleic acid" refers to a nucleic acid segment or fragment which has been separated from sequences which flank it in a naturally occurring state, e.g., a DNA fragment which has been removed from the sequences which are normally adjacent to the fragment, e.g., the sequences adjacent to the fragment in a genome in which it naturally occurs. The term also applies to nucleic acids which have been substantially purified from other components which naturally accompany the nucleic acid, e.g., RNA or DNA or proteins, which naturally accompany it in the cell. The term therefore includes, for example, a recombinant DNA which is incorporated into a vector, into an autonomously replicating plasmid or virus, or into the genomic DNA of a prokaryote or eukaryote, or which exists as a separate molecule (e.g., as a cDNA or a genomic or cDNA fragment produced by PCR or restriction enzyme digestion) independent of other sequences. It also includes a recombinant DNA which is part of a hybrid gene encoding additional polypeptide sequence.

Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

As used herein, a "detectable marker" or a "reporter molecule" is an atom or a molecule that permits the specific detection of a compound comprising the marker in the presence of similar compounds without a marker. Detectable markers or reporter molecules include, e.g., radioactive isotopes, antigenic determinants, enzymes, nucleic acids available for hybridization, chromophores, fluorophores, chemiluminescent molecules, electrochemically detectable molecules, and molecules that provide for altered fluorescence-polarization or altered light-scattering.

As used herein, a "ligand" is a compound that specifically binds to a target compound. A ligand (e.g., an antibody) "specifically binds to" or "is specifically immunoreactive with" a compound when the ligand functions in a binding reaction which is determinative of the presence of the compound in a sample of heterogeneous compounds. Thus, under designated assay (e.g., immunoassay) conditions, the ligand binds preferentially to a particular compound and does not bind to a significant extent to other compounds present in the sample. For example, an antibody specifically binds under immunoassay conditions to an antigen bearing an epitope against which the antibody was raised. A variety of immunoassay formats may be used to select antibodies specifically immunoreactive with a particular antigen. For example, solid-phase ELISA immunoassays are routinely used to select monoclonal antibodies specifically immunoreactive with an antigen. See Harlow and Lane, 1988, *Antibodies, A Laboratory Manual*, Cold Spring Harbor Publications, New York, for a description of immunoassay formats and conditions that can be used to determine specific immunoreactivity.

As used herein, the term "linkage" refers to a connection between two groups. The connection can be either covalent or non-covalent, including but not limited to ionic bonds, hydrogen bonding, and hydrophobic/hydrophilic interactions.

As used herein, the term "linker" refers to a molecule that joins two other molecules either covalently or noncovalently, e.g., through ionic or hydrogen bonds or van der Waals interactions.

The term "low adherence, ultra low adherence, or non-adherence surface for cell attachment" refers to the ability of a surface to support attachment of cells. The term "non-adherence surface for cell attachment" means that the surface supports little if any cell attachment.

Micro-RNAs are generally about 16-25 nucleotides in length. In one aspect, miRNAs are RNA molecules of 22 nucleotides or less in length. These molecules have been found to be highly involved in the pathology of several types of cancer. Although the miRNA molecules are generally found to be stable when associated with blood serum and its components after EDTA treatment, introduction of locked nucleic acids (LNAs) to the miRNAs via PCR further increases stability of the miRNAs. LNAs are a class of nucleic acid analogues in which the ribose ring is "locked" by a methylene bridge connecting the 2'-0 atom and the 4'-C atom of the ribose ring, which increases the molecule's affinity for other molecules. miRNAs are species of small non-coding single-stranded regulatory RNAs that interact with the 3'-untranslated region (3'-UTR) of target mRNA molecules through partial sequence homology. They participate in regulatory networks as controlling elements that direct comprehensive gene expression. Bioinformatics analysis has predicted that a single miRNA can regulate hundreds of target genes, contributing to the combinational and subtle regulation of numerous genetic pathways.

The term "modulate", as used herein, refers to changing the level of an activity, function, or process. The term "modulate" encompasses both inhibiting and stimulating an activity, function, or process. The term "modulate" is used interchangeably with the term "regulate" herein.

The terms "multicellular aggregate", "multicellular sphere", "blastema", and "multicellular structure" are used interchangeably herein.

The term "nucleic acid" typically refers to large polynucleotides. By "nucleic acid" is meant any nucleic acid, whether composed of deoxyribonucleosides or ribonucleosides, and whether composed of phosphodiester linkages or modified linkages such as phosphotriester, phosphoramidate, siloxane, carbonate, carboxymethylester, acetamidate, carbamate, thioether, bridged phosphoramidate, bridged methylene phosphonate, bridged phosphoramidate, bridged phosphoramidate, bridged methylene phosphonate, phosphorothioate, methylphosphonate, phosphorodithioate, bridged phosphorothioate or sulfone linkages, and combinations of such linkages. The term nucleic acid also specifically includes nucleic acids composed of bases other than the five biologically occurring bases (adenine, guanine, thymine, cytosine, and uracil).

As used herein, the term "nucleic acid" encompasses RNA as well as single and double-stranded DNA and cDNA. Furthermore, the terms, "nucleic acid," "DNA," "RNA" and similar terms also include nucleic acid analogs, i.e. analogs having other than a phosphodiester backbone. For example, the so-called "peptide nucleic acids," which are known in the art and have peptide bonds instead of phosphodiester bonds in the backbone, are considered within the scope of the present invention. By "nucleic acid" is meant any nucleic acid, whether composed of deoxyribonucleosides or ribonucleosides, and whether composed of phosphodiester linkages or modified linkages such as phosphotriester, phosphoramidate, siloxane, carbonate, carboxymethylester, acetamidate, carbamate, thioether, bridged phosphoramidate, bridged methylene phosphonate, bridged phosphoramidate, bridged phosphoramidate, bridged methylene phosphonate, phosphorothioate, methylphosphonate, phosphorodithioate, bridged phosphorothioate or sulfone linkages, and combinations of such linkages. The term nucleic acid also specifically includes nucleic acids composed of bases other than the five biologically occurring bases (adenine, guanine, thymine, cytosine, and uracil). Conventional notation is used herein to describe polynucleotide sequences: the left-hand end of a single-stranded polynucleotide sequence is the 5'-end; the left-hand direction of a double-stranded polynucleotide sequence is referred to as the 5'-direction. The direction of 5' to 3' addition of nucleotides to nascent RNA transcripts is referred to as the transcription direction. The DNA strand having the same sequence as an mRNA is referred to as the "coding strand"; sequences on the DNA strand which are located 5' to a reference point on the DNA are referred to as "upstream sequences"; sequences on the DNA strand which are 3' to a reference point on the DNA are referred to as "downstream sequences."

The term "nucleic acid construct," as used herein, encompasses DNA and RNA sequences encoding the particular gene or gene fragment desired, whether obtained by genomic or synthetic methods.

Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

The term "oligonucleotide" typically refers to short polynucleotides, generally, no greater than about 50 nucleotides. It will be understood that when a nucleotide sequence is represented by a DNA sequence (i.e., A, T, G, C), this also includes an RNA sequence (i.e., A, U, G, C) in which "U" replaces "T."

The term "otherwise identical sample", as used herein, refers to a sample similar to a first sample, that is, it is obtained in the same manner from the same subject from the same tissue or fluid, or it refers a similar sample obtained from a different subject. The term "otherwise identical sample from an unaffected subject" refers to a sample obtained from a subject not known to have the disease or disorder being examined. The sample may of course be a standard sample. By analogy, the term "otherwise identical" can also be used regarding regions or tissues in a subject or in an unaffected subject.

By describing two polynucleotides as "operably linked" is meant that a single-stranded or double-stranded nucleic acid moiety comprises the two polynucleotides arranged within the nucleic acid moiety in such a manner that at least one of the two polynucleotides is able to exert a physiological effect by which it is characterized upon the other. By way of example, a promoter operably linked to the coding region of a gene is able to promote transcription of the coding region.

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intraperitoneal, intramuscular, intrasternal injection, and kidney dialytic infusion techniques.

The term "progeny" of a stem cell as used herein refers to a cell which is derived from a stem cell and may still have all of the differentiation abilities of the parental stem cell, i.e., multipotency, or one that may no longer be multipotent, but is now committed to being able to differentiate into only one cell type, i.e., a committed cell type. The term may also refer to a differentiated cell.

The term "peptide" typically refers to short polypeptides.

The term "per application" as used herein refers to administration of cells, a drug, or compound to a subject.

The term "pharmaceutical composition" shall mean a composition comprising at least one active ingredient, whereby the composition is amenable to investigation for a specified, efficacious outcome in a mammal (for example, without limitation, a human). Those of ordinary skill in the art will understand and appreciate the techniques appropriate for determining whether an active ingredient has a desired efficacious outcome based upon the needs of the artisan.

As used herein, the term "pharmaceutically acceptable carrier" includes any of the standard pharmaceutical carriers, such as a phosphate buffered saline solution, water, emulsions such as an oil/water or water/oil emulsion, and various types of wetting agents. The term also encompasses any of the agents approved by a regulatory agency of the US Federal government or listed in the US Pharmacopeia for use in animals, including humans.

As used herein, the term "physiologically acceptable" ester or salt means an ester or salt form of the active ingredient which is compatible with any other ingredients of the pharmaceutical composition, which is not deleterious to the subject to which the composition is to be administered.

"Plurality" means at least two.

A "polynucleotide" means a single strand or parallel and anti-parallel strands of a nucleic acid. Thus, a polynucleotide may be either a single-stranded or a double-stranded nucleic acid.

"Polypeptide" refers to a polymer composed of amino acid residues, related naturally occurring structural variants, and synthetic non-naturally occurring analogs thereof linked via peptide bonds, related naturally occurring structural variants, and synthetic non-naturally occurring analogs thereof.

"Synthetic peptides or polypeptides" means a non-naturally occurring peptide or polypeptide. Synthetic peptides or polypeptides can be synthesized, for example, using an automated polypeptide synthesizer. Various solid phase peptide synthesis methods are known to those of skill in the art.

The term "prevent," as used herein, means to stop something from happening, or taking advance measures against something possible or probable from happening. In the context of medicine, "prevention" generally refers to action taken to decrease the chance of getting a disease or condition.

A "preventive" or "prophylactic" treatment is a treatment administered to a subject who does not exhibit signs, or exhibits only early signs, of a disease or disorder. A prophylactic or preventative treatment is administered for the purpose of decreasing the risk of developing pathology associated with developing the disease or disorder.

"Primer" refers to a polynucleotide that is capable of specifically hybridizing to a designated polynucleotide template and providing a point of initiation for synthesis of a complementary polynucleotide. Such synthesis occurs when the polynucleotide primer is placed under conditions in which synthesis is induced, i.e., in the presence of nucleotides, a complementary polynucleotide template, and an agent for polymerization such as DNA polymerase. A primer is typically single-stranded, but may be double-stranded. Primers are typically deoxyribonucleic acids, but a wide variety of synthetic and naturally occurring primers are useful for many applications. A primer is complementary to the template to which it is designed to hybridize to serve as a site for the initiation of synthesis, but need not reflect the exact sequence of the template. In such a case, specific hybridization of the primer to the template depends on the stringency of the hybridization conditions. Primers can be labeled with, e.g., chromogenic, radioactive, or fluorescent moieties and used as detectable moieties.

The term "progeny" of a stem cell as used herein refers to a cell which is derived from a stem cell and may still have all of the differentiation abilities of the parental stem cell, i.e., multipotency, or one that may no longer be multipotent, but is now committed to being able to differentiate into only one cell type, i.e., a committed cell type. The term may also refer to a differentiated cell.

As used herein, the term "promoter/regulatory sequence" means a nucleic acid sequence which is required for expression of a gene product operably linked to the promoter/regulator sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

A "constitutive" promoter is a promoter which drives expression of a gene to which it is operably linked, in a constant manner in a cell. By way of example, promoters which drive expression of cellular housekeeping genes are considered to be constitutive promoters.

An "inducible" promoter is a nucleotide sequence which, when operably linked with a polynucleotide which encodes or specifies a gene product, causes the gene product to be produced in a living cell substantially only when an inducer which corresponds to the promoter is present in the cell.

A "tissue-specific" promoter is a nucleotide sequence which, when operably linked with a polynucleotide which encodes or specifies a gene product, causes the gene product to be produced in a living cell substantially only if the cell is a cell of the tissue type corresponding to the promoter.

The term "propagate" means to reproduce or to generate.

As used herein, "protecting group" with respect to a terminal amino group refers to a terminal amino group of a peptide, which terminal amino group is coupled with any of various amino-terminal protecting groups traditionally employed in peptide synthesis. Such protecting groups include, for example, acyl protecting groups such as formyl, acetyl, benzoyl, trifluoroacetyl, succinyl, and methoxysuccinyl; aromatic urethane protecting groups such as benzyloxycarbonyl; and aliphatic urethane protecting groups, for example, tert-butoxycarbonyl or adamantyloxycarbonyl. See Gross and Mienhofer, eds., *The Peptides*, vol. 3, pp. 3-88 (Academic Press, New York, 1981) for suitable protecting groups.

As used herein, "protecting group" with respect to a terminal carboxy group refers to a terminal carboxyl group of a peptide, which terminal carboxyl group is coupled with any of various carboxyl-terminal protecting groups. Such protecting groups include, for example, tert-butyl, benzyl, or other acceptable groups linked to the terminal carboxyl group through an ester or ether bond.

The term "protein" typically refers to large polypeptides. Conventional notation is used herein to portray polypeptide sequences: the left-hand end of a polypeptide sequence is the amino-terminus; the right-hand end of a polypeptide sequence is the carboxyl-terminus.

The term "protein regulatory pathway", as used herein, refers to both the upstream regulatory pathway which regulates a protein, as well as the downstream events which that protein regulates. Such regulation includes, but is not limited to, transcription, translation, levels, activity, posttranslational modification, and function of the protein of interest, as well as the downstream events which the protein regulates.

The terms "protein pathway" and "protein regulatory pathway" are used interchangeably herein.

As used herein, the term "purified" and like terms relate to an enrichment of a molecule or compound relative to other components normally associated with the molecule or compound in a native environment. The term "purified" does not necessarily indicate that complete purity of the particular molecule has been achieved during the process. A "highly purified" compound as used herein refers to a compound that is greater than 90% pure.

"Recombinant polynucleotide" refers to a polynucleotide having sequences that are not naturally joined together. An amplified or assembled recombinant polynucleotide may be included in a suitable vector, and the vector can be used to transform a suitable host cell.

A recombinant polynucleotide may serve a non-coding function (e.g., promoter, origin of replication, ribosome-binding site, etc.) as well.

A host cell that comprises a recombinant polynucleotide is referred to as a "recombinant host cell." A gene which is expressed in a recombinant host cell wherein the gene comprises a recombinant polynucleotide, produces a "recombinant polypeptide."

A "recombinant polypeptide" is one which is produced upon expression of a recombinant polynucleotide.

The term "regulate" refers to either stimulating or inhibiting a function or activity of interest.

As used herein, term "regulatory elements" is used interchangeably with "regulatory sequences" and refers to promoters, enhancers, and other expression control elements, or any combination of such elements.

A "reversibly implantable" device is one which may be inserted (e.g. surgically or by insertion into a natural orifice of the animal) into the body of an animal and thereafter removed without great harm to the health of the animal.

A "sample," as used herein, refers preferably to a biological sample from a subject, including, but not limited to, normal tissue samples, diseased tissue samples, biopsies, blood, saliva, feces, semen, tears, and urine. A sample can also be any other source of material obtained from a subject which contains cells, tissues, or fluid of interest. A sample can also be obtained from cell or tissue culture.

As used herein, the term "secondary antibody" refers to an antibody that binds to the constant region of another antibody (the primary antibody).

By "small interfering RNAs (siRNAs)" is meant, inter alia, an isolated dsRNA molecule comprised of both a sense and an anti-sense strand. In one aspect, it is greater than 10 nucleotides in length. siRNA also refers to a single transcript which has both the sense and complementary antisense sequences from the target gene, e.g., a hairpin. siRNA further includes any form of dsRNA (proteolytically cleaved products of larger dsRNA, partially purified RNA, essentially pure RNA, synthetic RNA, recombinantly produced RNA) as well as altered RNA that differs from naturally occurring RNA by the addition, deletion, substitution, and/or alteration of one or more nucleotides.

As used herein, the term "solid support" when used in reference to a substrate forming a linkage with a compound, relates to a solvent insoluble substrate that is capable of forming linkages (preferably covalent bonds) with various compounds. The support can be either biological in nature, such as, without limitation, a cell or bacteriophage particle, or synthetic, such as, without limitation, an acrylamide derivative, agarose, cellulose, nylon, silica, or magnetized particles.

By the term "solid support suitable for maintaining cells in a tissue culture environment" is meant any surface such as a tissue culture dish or plate, or even a cover, where medium containing cells can be added, and that support can be placed into a suitable environment such as a tissue culture incubator for maintaining or growing the cells. This should of course be a solid support that is either sterile or capable of being sterilized. The support does not need to be one suitable for cell attachment.

The term "solid support is a low adherence, ultralow adherence, or non-adherence support for cell culture purposes" refers to a vehicle such as a bacteriological plate or a tissue culture dish or plate which has not been treated or prepared to enhance the ability of mammalian cells to adhere to the surface. It could include, for example, a dish where a layer of agar has been added to prevent cells from attaching. It is known to those of ordinary skill in the art that bacteriological plates are not treated to enhance attachment of mammalian cells because bacteriological plates are generally used with agar, where bacteria are suspended in the agar and grow in the agar.

By the term "specifically binds to", as used herein, is meant when a compound or ligand functions in a binding reaction or assay conditions which is determinative of the presence of the compound in a sample of heterogeneous compounds.

The term "standard," as used herein, refers to something used for comparison. For example, a standard can be a known standard agent or compound which is administered or added to a control sample and used for comparing results when measuring said compound in a test sample. Standard can also refer to an "internal standard," such as an agent or compound which is added at known amounts to a sample and is useful in determining such things as purification or recovery rates when a sample is processed or subjected to purification or extraction procedures before a marker of interest is measured.

The term "stimulate" as used herein, means to induce or increase an activity or function level such that it is higher relative to a control value. The stimulation can be via direct or indirect mechanisms. In one aspect, the activity or function is stimulated by at least 10% compared to a control value, more preferably by at least 25%, and even more preferably by at least 50%.

The term "stimulator" as used herein, refers to any composition, compound or agent, the application of which results in the stimulation of a process or function of interest, including, but not limited to, wound healing, angiogenesis, bone healing, osteoblast production and function, and osteoclast production, differentiation, and activity.

A "subject" of diagnosis or treatment is an animal, including a human. It also includes pets and livestock.

As used herein, a "subject in need thereof" is a patient, animal, mammal, or human, who will benefit from the method of this invention.

The term "substantially pure" describes a compound, e.g., a protein or polypeptide which has been separated from components which naturally accompany it. Typically, a compound is substantially pure when at least 10%, more preferably at least 20%, more preferably at least 50%, more preferably at least 60%, more preferably at least 75%, more preferably at least 90%, and most preferably at least 99% of the total material (by volume, by wet or dry weight, or by mole percent or mole fraction) in a sample is the compound of interest. Purity can be measured by any appropriate method, e.g., in the case of polypeptides by column chromatography, gel electrophoresis, or HPLC analysis. A compound, e.g., a protein, is also substantially purified when it is essentially free of naturally associated components or when it is separated from the native contaminants which accompany it in its natural state.

The term "substituent" as used in the phrase "other cells which are not substituents of the at least one self-organizing blastema" refers to substituent cells of the blastema. Therefore, a cell which is not a substituent of a self-organizing blastema can be a cell that is adjacent to the blastema and need not be a cell derived from a self-organizing blastema.

A "surface active agent" or "surfactant" is a substance that has the ability to reduce the surface tension of materials and enable penetration into and through materials.

The term "symptom," as used herein, refers to any morbid phenomenon or departure from the normal in structure, function, or sensation, experienced by the patient and indicative of disease. In contrast, a "sign" is objective evidence of disease. For example, a bloody nose is a sign. It is evident to the patient, doctor, nurse and other observers.

A "therapeutic" treatment is a treatment administered to a subject who exhibits signs of pathology for the purpose of diminishing or eliminating those signs.

A "therapeutically effective amount" of a compound is that amount of compound which is sufficient to provide a beneficial effect to the subject to which the compound is administered.

The use of the phrase "tissue culture dish or plate" refers to any type of vessel which can be used to plate cells for growth or differentiation.

The term "thermal injury" is used interchangeably with "thermal burn" herein.

"Tissue" means (1) a group of similar cells united to perform a specific function; (2) a part of an organism consisting of an aggregate of cells having a similar structure and function; or (3) a grouping of cells that are similarly characterized by their structure and function, such as muscle or nerve tissue.

The term "topical application," as used herein, refers to administration to a surface, such as the skin. This term is used interchangeably with "cutaneous application" in the case of skin. A "topical application" is a "direct application".

By "transdermal" delivery is meant delivery by passage of a drug through the skin or mucosal tissue and into the bloodstream. Transdermal also refers to the skin as a portal for the administration of drugs or compounds by topical application of the drug or compound thereto. "Transdermal" is used interchangeably with "percutaneous."

The term "transfection" is used interchangeably with the terms "gene transfer", "transformation," and "transduction", and means the intracellular introduction of a polynucleotide. "Transfection efficiency" refers to the relative amount of the transgene taken up by the cells subjected to transfection. In practice, transfection efficiency is estimated by the amount of the reporter gene product expressed following the transfection procedure.

As used herein, the term "transgene" means an exogenous nucleic acid sequence comprising a nucleic acid which encodes a promoter/regulatory sequence operably linked to nucleic acid which encodes an amino acid sequence, which exogenous nucleic acid is encoded by a transgenic mammal.

As used herein, the term "transgenic mammal" means a mammal, the germ cells of which comprise an exogenous nucleic acid.

As used herein, a "transgenic cell" is any cell that comprises a nucleic acid sequence that has been introduced into the cell in a manner that allows expression of a gene encoded by the introduced nucleic acid sequence.

The term to "treat," as used herein, means reducing the frequency with which symptoms are experienced by a patient or subject or administering an agent or compound to reduce the frequency with which symptoms are experienced. A "prophylactic" treatment is a treatment administered to a subject who does not exhibit signs of a disease or exhibits only early signs of the disease for the purpose of decreasing the risk of developing pathology associated with the disease.

As used herein, the term "treating" includes prophylaxis of the specific disorder or condition, or alleviation of the symptoms associated with a specific disorder or condition and/or preventing or eliminating said symptoms. A "prophylactic" treatment is a treatment administered to a subject who does not exhibit signs of a disease or exhibits only early signs of the disease for the purpose of decreasing the risk of developing pathology associated with the disease.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer or delivery of nucleic acid to cells, such as, for example, polylysine compounds, liposomes, and the like. Examples of viral vectors include, but are not limited to, adenoviral vectors, adeno-associated virus vectors, retroviral vectors, recombinant viral vectors, and the like. Examples of non-viral vectors include, but are not limited to, liposomes, polyamine derivatives of DNA and the like.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses that incorporate the recombinant polynucleotide.

As used herein, the term "wound" relates to a physical tear, break, or rupture to a tissue or cell layer. A wound may occur by any physical insult, including a surgical procedure or as a result of a disease, disorder condition.

Methods useful for the practice of the invention which are not described herein are also known in the art. Useful methods include those described in WO 2007/030652 (PCT/US2006/034915), WO 2007/019107 (PCT/US2006/029686), WO 2007/089798 (PCT/US2007/002572), and WO 2008/060374 (PCT US2007/021432), the methods of which are hereby incorporated by reference.

Embodiments

The present invention provides inhibitors of miRNA let-7b activity or levels. In one aspect, the inhibitors are nucleic acids, including nucleic acids where the nucleotides are modified and/or the ends of the nucleic acid are modified.

The potential for microRNA let-7b inhibitor and similar inhibitors to prevent or treat vaso-obliteration and stabilize aberrant neovascularization into functional vessels through increasing pericyte coverage on these vessels represents a fundamentally new approach in the treatment of proliferative disease and a great technological improvement over previous treatments.

The present invention further encompasses the use of inhibitors of miRNA let-7b other than nucleic acids, including antibodies and drugs. Useful antibodies can be directed against miRNA let 7b or a molecule in its signal transduction or regulatory pathway. Antibodies include, but are not limited to, monoclonal antibodies, chimeric antibodies, single chain fragments of antibodies, humanized antibodies, and biologically active homologs and derivatives thereof.

In one aspect, an inhibitor of the invention is one of the following: Antagomir let-7b (ant-let7b), LNA-Chl antisense of let-7b, LNA antisense let-7b, MOE antisense let-7b, truncated ant-let7b, LNA-Chl antisense let-7b mini, LNA antisense let-7b mini, and MOE antisense let-7b mini. These nucleic acids are all related to SEQ ID NOs:1 or 2 and some include various modifications as disclosed herein:

1. AntagomiR let-7b
Dy547-mA(*)mA(*)mCmCmAmCmAmCmAmCmC-mUmAmCmUmAmCmCmU(*)m C(*)mA(*)(3'-Chl)

2. AntagomiR let-7b Mini (Truncated Version)
mA(*)mA(*)mCmCmAmCmAmCmAmCmC(*)mU(*)mA(3'-Chl)

The sequence is anti-sense to let-7b. "m" indicates 2-O-Methyl moiety; * indicates Phosphorothioate and a cholesterol molecule at the 3'. Dy-547 is a fluorescent molecule useful for detection purposes.

3. LNA-Chl Anti-Sense let-7b
lAlAlClClAlClAlClAlAlClClUlAlClUlAlClClUlCA(3'-Chl)

4. LNA-Chl anti-sense let-7b mini
lAlAlClClAlClAlClAlAlClClUlAlClClUlA(3'-Chl)

"l" indicates LNA modification; (3'-Chl) is a cholesterol molecule at the 3'

5. LNA anti-sense let-7b
lAlAlClClAlClAlClAlAlClClUlAlClUlAlClClUlAlClUlA-lClClUlClA 6. LNA anti-sense let-7b mini
lAlAlClClAlClAlClAlAlClClUlAlClClUlA "l" indicates LNA modification.

7. MOE anti-sense let-7b
meAmeAmeCmeCmeAmeCmeAmeCmeAmeAmeCmeC-meUmeAmeCmeUmeAme CmeCmeUmeCmeA 8. MOE anti-sense let-7b mini
meAmeAmeCmeCmeAmeCmeAmeCmeAmeAmeCmeC-meUmeA "me" indicates 2'-O-methoxyethyl modification.

It can be seen that various types of modifications can be made to a useful nucleic acid of the invention and that the modifications can be used in various combinations.

In one embodiment, the present invention provides for the administration of at least one miRNA, including pre-miRNA and mature miRNA, or a mimic thereof. "miRNA mimics" are chemically synthesized nucleic acid based molecules, and in one aspect are double-stranded RNAs which mimic mature endogenous miRNAs after transfection into cells.

Doses can vary depending on how and where they are administered and the age, sex, weight and health of the subject. For example, in mice, 1.5 µl to 2.0 µl of total volume of microRNA mimic or antagomiRs (1.7-3.4 µg/µl) was used in some instances. Useful ranges also include, but are not limited to about 0.1 to about 20.0 µg/µl in mice, or about 0.5 to about 15, or about 1.0 to about 10.0, or about 1.5 to about 8.0, or about 1.7 to about 5.0, or about 2.0 to about 4, or about 2.5 to about 3.0 µg/µl. Total volume and concentrations can be varied depending on the particular subject and the particular vascular disease or retinopathy being treated.

Let7, one of the founding members of the miRNA family, was first identified in *C. elegans*. There are several human homologs of *C. elegans* let7, and all of these LET7 miRNAs share an identical seed sequence critical for target recognition. Among the human LET7 miRNAs, LET7B and LET7E are most divergent, with differences in 4 nucleotides. In human, mouse, and *C. elegans*, expression of LET7 is barely detectable in embryonic stages, but it increases after differentiation and in mature tissues.

Using a directional cloning procedure to clone miRNAs from HeLa cell total RNA, Lagos-Quintana identified 9 human homologs of *C. elegans* let7, including LET7B. The LET7B sequence is UGAGGUAGUAGGUUGUGUGGUU (SEQ ID NO:7; Accession number MIMAT0001760).

miRNAs are transcribed by RNA polymerase II (pol II) or RNA polymerase III and arise from initial transcripts, termed primary miRNA transcripts (pri-miRNAs), that are generally several thousand bases long. Pri-miRNAs are processed in the nucleus by the RNase Drosha into about 70- to about 100-nucleotide hairpin-shaped precursors (pre-miRNAs). Following transport to the cytoplasm, the hairpin pre-miRNA is further processed by Dicer to produce a double-stranded miRNA. The mature miRNA strand is then incorporated into the RNA-induced silencing complex (RISC), where it associates with its target mRNAs by base-pair complementarity. In the relatively rare cases in which a miRNA base pairs perfectly with an mRNA target, it promotes mRNA degradation. More commonly, miRNAs form imperfect heteroduplexes with target mRNAs, affecting either mRNA stability or inhibiting mRNA translation.

In one aspect, an agonist as used herein is a molecule or compound that enhances the expression, levels, or activity of a target miRNA. In one aspect, an antagonist is one that inhibits the expression, levels, or activity of a target miRNA.

An administered miRNA may be the naturally occurring miRNA or it may be an analogue or homologue of the miRNA. In one aspect, the miRNA, or analogue or homologues, are modified to increase the stability thereof in the cellular milieu. In an alternative aspect, the miRNA is encoded by an expression vector and may be delivered to the target cell in a liposome or microvesicle.

In one embodiment, the antagonist is administered to a subject by intravenous injection. In one aspect, the antagonist is administered directly to the site of the disease, disorder or condition and the associated ischemia.

In one aspect, an miR-specific inhibitor may be an anti-miRNA (anti-miR) oligonucleotide (for example, see WO2005054494).

In one embodiment, the antagonist is administered to a subject by oral, intravenous, intramuscular, transdermal, sustained release, controlled release, delayed release, suppository, subcutaneous, catheter, topical, or sublingual administration.

In one aspect, a nucleic acid of the invention comprises a 3' cholesterol.

In one aspect, a nucleic acid of the invention comprises one or more phosphorothioates. In one aspect, a lower case subscript "s" can be used to indicate the position of the phosphorothioate.

In one aspect, a nucleic acid sequence of the invention has a 3' TT overhang.

In one aspect, it is dTdT.

In one aspect, a nucleic acid sequence of the invention has a UU overhang.

In one aspect, a sequence is modified with a 5' phosphate.

In one aspect, a sequence is modified with a biotin (BIO).

In one embodiment, the antagonist of the invention may be expressed in vivo from a vector. A "vector" is a composition of matter which can be used to deliver a nucleic acid of interest to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. Examples of viral vectors include, but are not limited to, adenoviral vectors, adeno-associated virus vectors, retroviral vectors, and the like. An expression construct can be replicated in a living cell, or it can be made synthetically. For purposes of this application, the terms "expression construct," "expression vector," and "vector," are used interchangeably to demonstrate the application of the invention in a general, illustrative sense, and are not intended to limit the invention.

The present invention relates to compositions and methods for treating microvascular injuries, diseases, or disorders where an increase in a miRNA of the let-7 family is associated with the injury, disease, or disorder. These include, but are not limited to, let-7b, let-7c-5p and let-7i-5p.

Some retinal diseases, disorders, and injuries include, for example, diabetic retinopathy, retinopathy, arteriosclerotic retinopathy, hypertensive retinopathy, proliferative vitreo-retinopathy, retinal tears, retinal detachment, macular degeneration, age related macular degeneration, inflammatory retinal disease, retinal vasculitis, retinal microvasculature disease, retinal fibrosis, diffuse unilateral subacute neuroretinitis, cytomegalovirus retinitis, Stargardts, Best's Disease, Usher Syndrome, papilloedema, injury, surgical/treatment side effect, vitelliform maculopathy, retinitis pigmentosa, cone-rod dystrophy, retinal separation, retinal hypoxia, aberrant neovascularization of the retina, retinal scar formation, and retinoblastoma. In one aspect, the retinal disease, disorder, or injury prevented or treated in is diabetic retinopathy. In one aspect, the disease or disorder is retinal degenerative disease, particularly degenerative retinopathy.

The compositions and methods of the invention are also useful for branch retinal vein or artery occlusion, as well as that of the central retinal artery and vein.

Debilitating retinopathies can involve progressive cellular degeneration leading to vision loss and blindness. These include, for example, diabetic retinopathy and choroidal neovascular membrane (CNVM). In one aspect, diabetic retinopathy may be classified as: 1) non-proliferative or background retinopathy, characterized by increased capillary permeability, edema, hemorrhage, microaneurysms, and exudates; or 2) proliferative retinopathy, characterized by neovascularization extending from the retina to the vitreous, scarring, fibrous tissue formation, and potential for retinal detachment.

In CNVM, abnormal blood vessels stemming from the choroid grow up through the retinal layers. The fragile new vessels break easily, causing blood and fluid to pool within the layers of the retina.

In another embodiment, the methods of the present invention may be used to prevent or treat macular degeneration. In one embodiment, macular degeneration is characterized by damage to or breakdown of the macula, which in one embodiment, is a small area at the back of the eye. In one embodiment, macular degeneration causes a progressive loss of central sight, but not complete blindness. In one embodiment, macular degeneration is of the dry type, while in another embodiment, it is of the wet type. In one embodiment, the dry type is characterized by the thinning and loss of function of the macula tissue. In one embodiment, the wet type is characterized by the growth of abnormal blood vessels behind the macula. In one embodiment, the abnormal blood vessels hemorrhage or leak, resulting in the formation of scar tissue if untreated. In some embodiments, the dry type of macular degeneration can turn into the wet type. In one embodiment, macular degeneration is age-related, which in one embodiment is caused by an ingrowth of choroidal capillaries through defects in Bruch's membrane with proliferation of fibrovascular tissue beneath the retinal pigment epithelium.

In another embodiment, the methods of the present invention may be used to prevent or treat retinopathy. In one embodiment, retinopathy refers to a disease of the retina, which in one embodiment is characterized by inflammation and in another embodiment, is due to blood vessel damage inside the eye. In one embodiment, retinopathy is diabetic retinopathy which, in one embodiment, is a complication of diabetes that is caused by changes in the blood vessels of the retina. In one embodiment, blood vessels in the retina leak blood and/or grow fragile, brush-like branches and scar tissue, which in one embodiment, blurs or distorts the images that the retina sends to the brain. In another embodiment, retinopathy is proliferative retinopathy, which in one embodiment, is characterized by the growth of new, abnormal blood vessels on the surface of the retina (neovascularization). In one embodiment, neovascularization around the pupil increases pressure within the eye, which in one embodiment, leads to glaucoma. In another embodiment, neovascularization leads to new blood vessels with weaker walls that break and bleed, or cause scar tissue to grow, which in one embodiment, pulls the retina away from the back of the eye (retinal detachment). In one embodiment, the pathogenesis of retinopathy is related to non-enzymatic glycation, glycoxidation, accumulation of advanced glycation end-products, free radical-mediated protein damage, up-regulation of matrix metalloproteinases, elaboration of growth factors, secretion of adhesion molecules in the vascular endothelium, or a combination thereof.

In one embodiment, retinopathy leads to macular edema, which in one embodiment, is swelling of the retina. In one embodiment, macular edema is characterized by retinal blood vessels that develop tiny leaks, which in one embodiment, allow blood and fluid to seep from the retinal blood vessels, and fatty material (called exudate) to deposit in the retina. In one embodiment, symptoms of macular edema comprise impaired or blurred vision.

In another embodiment, retinopathy refers to retinopathy of prematurity (ROP), which in one embodiment, occurs in premature babies when abnormal blood vessels and scar tissue grow over the retina. In one embodiment, retinopathy of prematurity is caused by a therapy necessary to promote the survival of a premature infant.

In another embodiment, retinopathy refers to arteriosclerotic retinopathy, which in one embodiment, is due to arteriosclerosis (hardening of the arteries). In another embodiment, retinopathy refers to hypertensive retinopathy, which in one embodiment, is due to high blood pressure. In another embodiment, retinopathy refers to solar retinopathy, while in another embodiment it refers to drug-related retinopathy.

In another embodiment, the methods of the present invention may be used to prevent or treat retinal detachment, including, inter alia, rhegmatogenous, tractional, or exudative retinal detachment, which in one embodiment, is the separation of the retina from its supporting layers. In one embodiment, retinal detachment is associated with a tear or hole in the retina through which the internal fluids of the eye may leak. In one embodiment, retinal detachment is caused by trauma, the aging process, severe diabetes, an inflammatory disorder, neovascularization, or retinopathy of prematurity, while in another embodiment, it occurs spontaneously. In one embodiment, bleeding from small retinal blood vessels may cloud the vitreous during a detachment, which in one embodiment, may cause blurred and distorted images. In one embodiment, a retinal detachment can cause severe vision loss, including blindness.

The development of diabetic retinopathy, which is characterized by vascular changes of the retinal capillary bed, is directly linked to the severity of hyperglycemia. The development of retinal capillary changes (microangiopathies) includes the appearance of the following histopathological and clinical lesions: selective pericyte loss, capillary basement membrane thickening, dilations/endothelial hypertrophy, permeability/hard exudates, capillary nonperfusion and occlusion/acellularity, microaneurysms/intraretinal hemorrhages, intraretinal microvascular abnormalities, ORMA shunts/dilated meshwork, cotton wool spots/ischemia, vessel-glial proliferation, extra retinal hemorrhages, glial-vitreal contraction, and macular edema. While many of these lesions are present in a number of ocular diseases, all of above-described lesions are only present together in DM.

Diabetic retinopathy includes the selective death of retinal capillary pericytes (mural cells or intramural pericytes). Exposure of pericytes to excess glucose or galactose results in apoptosis. The development and progression of diabetic retinopathy in both human patients and in dogs requires years to develop. This development is accelerated in galactosemic animals. For example, while retinopathy in diabetic dogs rarely progresses past the mild to moderate non-proliferative stage, retinal changes in galactose-fed dogs progress to the proliferative stage in essentially the same time period. The development and progression of diabetic retinopathy can be directly linked to hyperglycemic control.

The present invention encompasses, inter alia, treatment of retinopathies resulting from diabetes, preventative therapy for premature infants, regeneration of damaged retinas from ischemia/reperfusion injuries (retinal artery or vein occlusion), regeneration of ocular vascular tissue from trauma, treatment of retinal vascular damage due to retinal hypertension, treatment of age-related macular degeneration, treatment of anterior segment and cornea and sclera vasculopathies, and treatment of choroidal vasculopathies.

Retinal neovascularization that occurs in diabetic retinopathy results in collections of aberrant and immature retinal vessels. These vessels lack adequate perivascular support cells and thus are subject to destabilization and changes in growth factor concentration levels. Progression of neovascularization leads to vitreous hemorrhage and fibrovascular scarring which causes loss of vision. Neovascularization is a programmed response to retinal ischemia, but lacks the needed vessel maturation to stabilize them into functional blood vessels.

One of ordinary skill in the art will appreciate that the amount of agent used can vary, depending on such factors as the source of the cells used, the age of the subject, the health of the subject, and the agent used. In one aspect, cells are contacted with an agent at a concentration ranging from about 0.1 µg/ml to about 10 mg/ml. In one aspect, the range is from about 1.0 µg/ml to about 1.0 mg/ml. In one aspect, about 1.0 µg/ml of enhancing agent is used.

Based on the results disclosed herein, the compositions and methods of the invention can be used to treat microvasculature injuries, diseases, and disorders other than retinal injuries, diseases, or disorders. That is, the compositions and methods of the invention can be used to treat microvasculature injuries, diseases, and disorders of other types of tissues where there is an associated deleterious increase in a miRNA, particularly a let-7 family miRNA.

Pharmaceutical compositions comprising the present cells, conditioned medium, or compounds are administered to an individual in need thereof by any number of routes including, but not limited to, intraocular, intravitreal, subretinal, topical, oral, intravenous, intramuscular, intra-arterial, intramedullary, intrathecal, intraventricular, transdermal, subcutaneous, intraperitoneal, intranasal, enteral, topical, sublingual, or rectal means.

The present invention is also directed to pharmaceutical compositions comprising the peptides of the present invention. More particularly, such compounds can be formulated as pharmaceutical compositions using standard pharmaceutically acceptable carriers, fillers, solublizing agents and stabilizers known to those skilled in the art.

The invention also encompasses the use pharmaceutical compositions of an appropriate compound, homolog, fragment, analog, or derivative thereof to practice the methods of the invention, the composition comprising at least one appropriate compound, homolog, fragment, analog, or derivative thereof and a pharmaceutically-acceptable carrier.

The pharmaceutical compositions useful for practicing the invention may be administered to deliver a dose of between 1 ng/kg/day and 100 mg/kg/day. Pharmaceutical compositions that are useful in the methods of the invention may be administered systemically in oral solid formulations, ophthalmic, suppository, aerosol, topical or other similar formulations. In addition to the appropriate compound, such pharmaceutical compositions may contain pharmaceutically-acceptable carriers and other ingredients known to enhance and facilitate drug administration. Other possible formulations, such as nanoparticles, liposomes, resealed erythrocytes, and immunologically based systems may also be used to administer an appropriate compound according to the methods of the invention.

Compounds which are identified using any of the methods described herein may be formulated and administered to a subject for treatment of the diseases disclosed herein.

The invention encompasses the preparation and use of pharmaceutical compositions comprising a compound useful for treatment of the conditions, disorders, and diseases disclosed herein as an active ingredient. Such a pharmaceutical composition may consist of the active ingredient alone, in a form suitable for administration to a subject, or the pharmaceutical composition may comprise the active ingredient and one or more pharmaceutically acceptable carriers, one or more additional ingredients, or some combination of these. The active ingredient may be present in the pharmaceutical composition in the form of a physiologically acceptable ester or salt, such as in combination with a physiologically acceptable cation or anion, as is well known in the art.

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

Although the descriptions of pharmaceutical compositions provided herein are principally directed to pharmaceutical compositions which are suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation.

Subjects to which administration of the pharmaceutical compositions of the invention is contemplated include, but are not limited to, humans and other primates, mammals including commercially relevant mammals such as cattle, pigs, horses, sheep, cats, and dogs, birds including commercially relevant birds such as chickens, ducks, geese, and turkeys.

Pharmaceutical compositions that are useful in the methods of the invention, depending on the injury, disease, or disorder being treated, may be prepared, packaged, or sold in formulations suitable for, including, but not limited to, intravitreal, oral, rectal, vaginal, parenteral, topical, pulmonary, intranasal, buccal, ophthalmic, intrathecal or another route of administration. Other contemplated formulations include projected nanoparticles, liposomal preparations, resealed erythrocytes containing the active ingredient, and immunologically-based formulations.

A pharmaceutical composition of the invention may be prepared, packaged, or sold in bulk, as a single unit dose, or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient.

In addition to the active ingredient, a pharmaceutical composition of the invention may further comprise one or more additional pharmaceutically active agents. Particularly contemplated additional agents include anti-emetics and scavengers such as cyanide and cyanate scavengers.

Examples of antimicrobial agents that can be used in the present invention include, but are not limited to, isoniazid, ethambutol, pyrazinamide, streptomycin, clofazimine, rifabutin, fluoroquinolones, ofloxacin, sparfloxacin, rifampin, azithromycin, clarithromycin, dapsone, tetracycline, erythromycin, cikprofloxacin, doxycycline, ampicillin, amphotericine B, ketoconazole, fluconazole, pyrimethamine, sulfadiazine, clindamycin, lincomycin, pentamidine, atovaquone, paromomycin, diclarazaril, acyclovir, trifluorouridine, foscarnet, penicillin, gentamicin, ganciclovir, iatroconazole, miconazole, Zn-pyrithione, and silver salts, such as chloride, bromide, iodide, and periodate.

In one embodiment, the biologically active agents or compounds can first be encapsulated into microcapsules, microspheres, microparticles, microfibers, reinforcing fibers and the like to facilitate mixing and achieving controlled, extended, delayed and/or sustained release and combined with the cells of the invention. Encapsulating the biologically active agent can also protect the agent against degradation during formation of the composite of the invention.

The present invention further provides for differentiating a subject in need of treatment with an inhibitor of miRNA let-7b from one who does not by measuring the levels of miRNA let-7b in the subject. When the levels are increased relative to a control value such as a standard or to prior levels in the subject, then a treatment regimen can be designed to administer one or more inhibitors of miRNA let-7b. Therefore, the present invention encompasses establishing a treatment regimen for a subject with retinopathy. In one aspect, the retinopathy is diabetic retinopathy.

The present invention provides compositions and methods for monitoring the progression of retinopathy in a subject by detecting and measuring the levels of miRNA let-7b. In one aspect, the subject is one not being treated, but who is susceptible to retinopathy or has early signs or symptoms of retinopathy. In one aspect, the subject is one being treated being for retinopathy associated with increased levels or activity of miRNA let-7b and the subject is monitored during treatment by detecting and measuring the levels and/or activity of miRNA let-7b and comparing the levels to a standard or to earlier activity or levels. In one aspect, the method is also useful for developing or modifying a treatment regimen based on the levels of miRNA let-7b that are detected or changes that are seen during treatment.

The invention also includes a kit comprising the composition of the invention and an instructional material which describes administering or using the composition. In another embodiment, this kit comprises a (preferably sterile) solvent suitable for dissolving or suspending the composition of the invention prior to administering the composition. Optionally, at least one growth factor and/or antimicrobial agent may be included in the kit.

Without further description, it is believed that one of ordinary skill in the art can, using the preceding description and the following illustrative examples, make and utilize the compounds of the present invention and practice the claimed methods. The following examples therefore, specifically point out the preferred embodiments of the present invention, and are not to be construed as limiting in any way the remainder of the disclosure.

Examples

It is disclosed herein that injection of a microRNA let-7b inhibitor will reduce retinal capillary dropout, diminish microvascular leakage, and prevent hyperproliferation of microvascular cells in murine models that develop pathology similar to that found in human diabetic retinopathy.

The approach disclosed herein focuses on both early and late disease intervention through vasculature stabilization of existing vessels at early time points and proliferative neovessels once disease has progressed.

Materials and Methods:
The Chemical Structures of Some let-7b Inhibitors—
Provided above are useful sequences for inhibiting miRNA let-7b. They are related to SEQ ID NOs: 1 and 2.

The microRNA let-7b inhibitor (Dy547-mA(*)mA(*)mCmCmAmCmAmCmAmAmCmCmUmAmCmUmAm-CmCmU(*)m C(*)mA (*)(3'-Chl)), was custom made and purchased from Dharmacon.

Depending on the particular experiment and the result being achieved, microRNA let-7b inhibitor was injected in mice at 1.7 to 3.4 µg/µl for a total volume of 2.0 µl per eye (3.4 to 6.8 µg total inhibitor). Similar concentrations can be used in the eyes of other types of animals and the volume and total amounts can be adjusted accordingly based on the size of the eye.

Four sequences are described further in detail FIG. 12, as are any modifications, etc. They represent the two sequences (first strand and complementary strand) for let-7b and a control miR (GLs). Each molecule is double stranded, thus the total of four different sequences seen above and in FIG. 12.

Modified sequences include: Antagomir let-7b (ant-let7b), LNA-Chl antisense of let-7b, LNA antisense let-7b, MOE antisense let-7b, truncated ant-let7b, LNA-Chl antisense let-7b mini, LNA antisense let-7b mini, and MOE antisense let-7b mini. These nucleic acids are all related to SEQ ID NOs: 1 or 2 and some include various modifications as illustrated below:

1. AntagomiR let-7b
Dy547-mA(*)mA(*)mCmCmAmCmAmCmAmAmCmC-mUmAmCmUmAmCmCmU(*)m C(*)mA(*)(3'-Chl)

2. AntagomiR Let-7b Mini (Truncated Version)
mA(*)mA(*)mCmCmAmCmAmCmAmAmCmC(*)mU(*) mA(3'-Chl)

The sequence is anti-sense to let-7b. "m" indicates 2-O-Methyl moiety; * indicates Phosphorothioate and a cholesterol molecule at the 3'. Dy-547 is a fluorescent molecule for detection.

3. LNA-Chl Anti-Sense let-7b
lAlAlClClAlClAlClAlAlClClUlAlClUlAlClClUlClA(3'-Chl)

4. LNA-Chl Anti-Sense let-7b Mini
lAlAlClClAlClAlClAlAlClClUlAlClClUlA(3'-Chl)
"l" indicates LNA modification; (3'-Chl) is a cholesterol molecule at the 3'

5. LNA Anti-Sense let-7b
lAlAlClClAlClAlClAlAlClClUlAlClUlAlClClUlAlClUlA-lClClUlClA 6. LNA Anti-Sense let-7b Mini
lAlAlClClAlClAlClAlAlClClUlAlClClUlA
"l" indicates LNA modification.

7. MOE Anti-Sense let-7b
meAmeAmeCmeCmeAmeCmeAmeCmeAmeAmeCmeC-meUmeAmeCmeUmeAme CmeCmeUmeCmeA 8. MOE Anti-Sense let-7b Mini
meAmeAmeCmeCmeAmeCmeAmeCmeAmeAmeCmeC-meUmeA
"me" indicates 2'-O-methoxyethyl modification.

Materials:
Akimba Mouse Model: The mechanisms of progression of advanced diabetic retinopathy (DR) mostly remain unknown due to lack of an appropriate animal model. We have overcome these limitations by using the recently developed Akimba mouse model (Ins2Akita VEGF+/−), which recapitulates most of the phenotypes of human severe non-proliferative and proliferative DR (NPDR/PDR). Akimba mouse model is a genetic cross between the Kimba (VEGF+/−) line and the diabetic Ins2Akita line. Kimba (VEGF+/−) line triggers chronic progressive retinal ischemia by transiently overexpressing human VEGF in retinal photoreceptors, and hyperglycemic Ins2Akita line that further causes additional damage to the retinal vasculature and cell types (FIG. 3A,B). The Akimba mouse serves as an excellent model system for studying retinal vasculature protection as our group recently showed that adipose derived stem cells (ASCs) can stabilize Akimba microvasculature. Inventors are maintaining an Akimba colony and our extensive experience with Akimba line will allow us to successfully accomplish our goal.

Antibodies:

Various monoclonal and polyclonal antibodies used in these studies were purchased commercially.

Molecular and Cell Culture Reagents:

Various molecular and cell culture materials such as culture media, RNA isolation reagents, cDNA synthesis kits, quantitative RT-PCR kit, Sybr green, buffers, other chemicals and reagents used in these studies were purchased commercially. Inventors designed RT-PCR primer and siRNAs using specific software and custom made from these from Life Technologies. Inventors designed antagomiRs and 2-O-Me antisense microRNAs and purchased them from Dharmacon.

Methods:

Cell Culture and Transfection of siRNA, microRNA Mimic, and microRNA Inhibitors:

Various siRNAs, microRNA mimics, and microRNA inhibitors were transfected into different cells using RNAiMAX (Invitrogen) by following the manufacturer's instructions.

RNA Isolation, cDNA Synthesis, and Quantitative RT-PCR:

Various cells were collected at different days of culture. Total RNA was extracted using Trizol reagent (Invitrogen) by following the manufacturer's instructions. Ncode microRNA first-strand cDNA synthesis and a quantitative reverse transcriptase PCR (qRT-PCR) kit (Invitrogen) were used to perform RT-PCR for microRNA detection. For mRNA detection, cDNA synthesis was carried out using the Superscript III first-strand synthesis system for RT-PCR (Invitrogen). Then, quantitative PCR (qPCR) was carried out using Sybr green PCR master mix in an ABI cycler, or BioRad CFX. ABI or BioRad software was used for quantification.

Microarray Profiling of microRNA:

Total RNA was extracted from WT and Akimba retinas separately using Trizol reagent as described. The samples were further purified using a Qiagen RNA column, and each sample was send to Exiqon. Microarray profiling of microRNA was carried out in a locked nucleic acid-based platform by Exiqon.

Luciferase Reporter Assays:

Human retinal pericyte cells were transfected with let-7b using RNAiMAX transfection reagent twice in a 24-h interval. Six hours after the last transfection, luciferase plasmids were transfected using Lipofectamine 2000. Control vector pGL3 (Promega) was transfected as an internal control. At 48 h after plasmid transfection, luciferase assays were performed with the Dual-Luciferase reporter assay system (Promega) by following the manufacturer's instructions. Each value from the *Renilla* luciferase construct (rr) was first normalized to the firefly (*Photinus pyralis*) luciferase value (pp) from the cotransfected pGL3 control vector. Each rr/pp value in the microRNA transfections was again normalized to the rr/pp value obtained in control GL2-transfected cells.

Immunocytochemistry:

Immunostaining was performed using the standard protocol established in the lab. The confocal LSM 700 microscopy was used to capture images.

Western Blotting:

Cells were lysed in lysis buffer (50 mM Tris-HCl, 150 mM NaCl, 0.1% NP-40, 5 mM EDTA, 10% glycerol) supplemented with protease inhibitor mix (Sigma). Proteins were resolved by SDS-PAGE, transferred either semi-dry or wet transfer, and immunoblotted with various antibodies.

Intravitreal Injection:

Mice were anesthetized with ketamine/xylazine injected intraperitoneally. 1.5 µl to 2.0 µl of total volume of microRNA mimic ( ) or antagomiRs (1.7-3.4 µg/µl) were injected intravitreally following our standard procedures. Doses can be extrapolated for human use.

Results:

Let-7b Expression is Upregulated in the Retina During Diabetic Retinopathy of Akimba Mouse Model.

Figure 2:
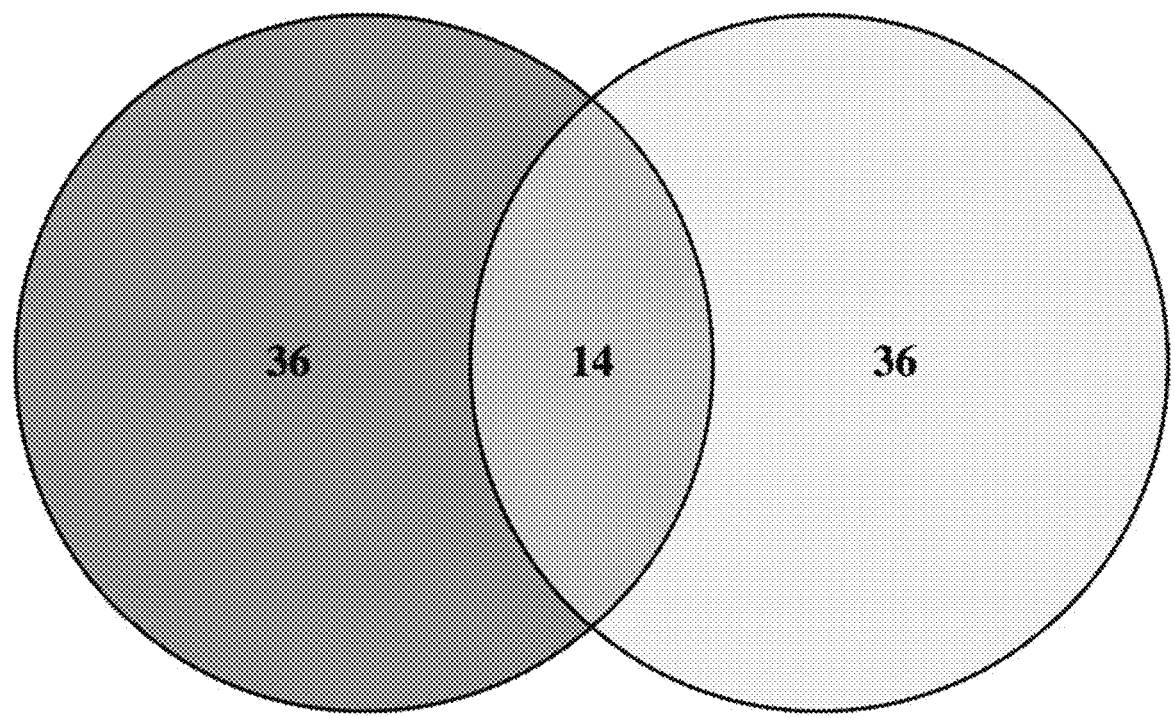
FIG. 2: Common microRNAs among Akimba and human proliferative diabetic retinopathy (PDR) samples. Top 50 differentially expressed microRNAs were intersected among Akimba and human PDR samples; let-7b was up-regulated in both the sample.

Genome wide profiling of microRNAs from the small RNA samples of Wild Type (WT) and Akimba retinas was performed. The data reveal that 34 microRNAs were upregulated and 16 microRNAs were downregulated in Akimba retinas. A subset of these upregulated microRNAs including let-7b, a let-7 family microRNA exhibited substantial overlap with upregulated microRNAs in vitreous of patients of advanced diabetic retinopathy, also known as proliferative diabetic retinopathy (PDR) (FIG. 2; 3C, D). Further studies were performed to understand the function of let-7b because (i) let-7b significantly overlaps with that of human PDR, (ii) let-7b is a well-established regulator of glucose metabolism, and (iii) polymorphisms in let-7b are associated with increased risk of type 2 diabetes. These studies strongly suggest a major role of let-7b in progression of DR.

let-7b miRNA is not the only let-7 member to increase in Akimba retinas. Ongoing microarray studies outlined above demonstrate that let-7c-5p and let-7i-5p are upregulated significantly in the Akimba retinas (data not shown).

Autophagy is Induced in the Retina of Diabetic Retinopathy.

Figure 5A:
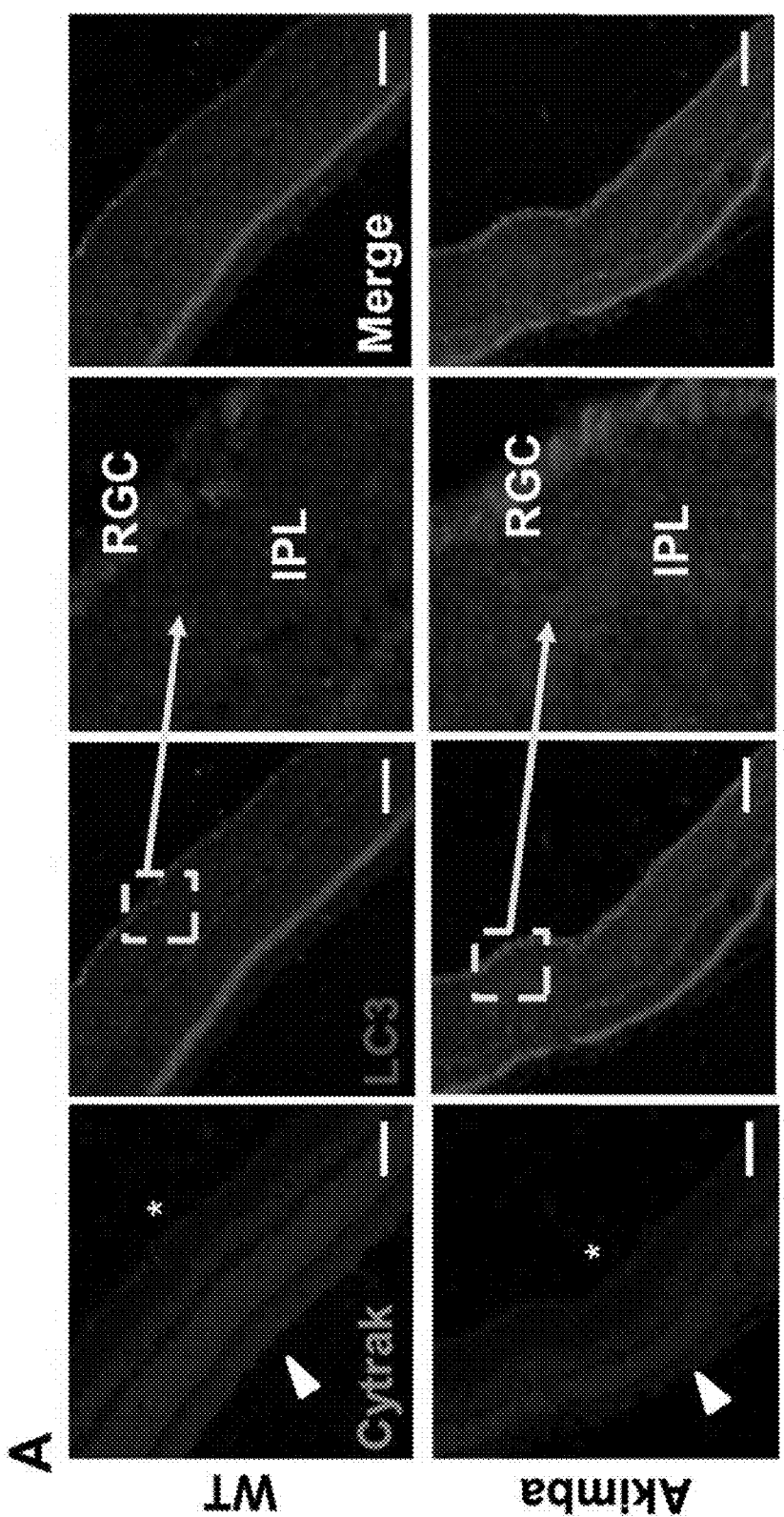

Autophagy is a multi-step process that involves large number of proteins and signaling molecules. Two important steps are the formation of autophagosome, a double-layered lipid structure around the damaged cellular components and fusion of autophagosome with lysosomes for degradation. LC3II, a lipidated form of a microtubule-associated protein called LC3 increases and p62, also known as sequestosome 1 decreases during autophagy. The critical role of autophagy in diverse biological process including cellular differentiation, development, and disease has been reported. Dysregulation of autophagy been reported in human degenerative disease. However, the role of autophagy and its molecular pathways in DR is not understood well. Let-7b microRNAs are up-regulated in Akimba retina and PDR patients' eyes and let-7b upregulates autophagy in neuronal cells suggesting dysregulated autophagy contributes to progression of DR. To confirm autophagy status, autophagy markers were measured in Akimba retina. LC3 is highly expressed in the superficial retinal vasculature and RGCs of Akimba retina (FIG. 4A). LC3 was higher in the retinal vasculature/RGCs of the superficial plane of Akimba mice. p62 is expected to decrease with induction of autophagy. In fact, p62 was decreased in the superficial retinal vasculature of Akimba mice (FIG. 4B). The superficial vasculature plane of Akimba retinas showed decreased p62 expression in the RGC/interstitial space and retinal vasculature when compared to age-matched WT retina (FIG. 4B). Interestingly, LC3 is increased in the areas of DR retinas where let-7b is upregulated (FIG. 5). LC3 expression was higher in the retinal ganglion cell (RGC) and inner plexiform layer (IPL) of Akimba retina (FIG. 5).

Let-7b Induces Autophagy in Human Retinal Pericytes and Mouse Retina.

To prove directly whether let-7b induces autophagy, let-7b and GFP-LC3b were transfected into human retinal pericytes. let-7b induces autophagy in human retinal pericytes as marked by transfected GFP-LC3b puncta (FIG. 6A). Further, Western blot demonstrates let-7b transfection induces endogenous autophagy markers in human retinal pericytes (FIG. 6B). Intravitreal injection of let-7b induced autophagy in the retina of WT mice (FIG. 6C).

Let-7b Induces Autophagy by Directly Targeting and Downregulating the Genes Upstream of mTORC1 and FoxO3A Pathway.

It was completely unknown how let-7b exerts its role in progression of DR and the present experiments were initiated by identifying direct targets and signaling pathways. The resulting data demonstrate that HMGA2 is a direct target of let-7b in retinal pericytes (FIG. 7C, D). let-7b decreases both HMGA2, Igf1r and IGFBP2 in vitro and in Akimba retina in vivo (FIG. 7A-B). Surprisingly, knock down of HMGA2 induces autophagy markers (FIG. 7E).

Figure 8:
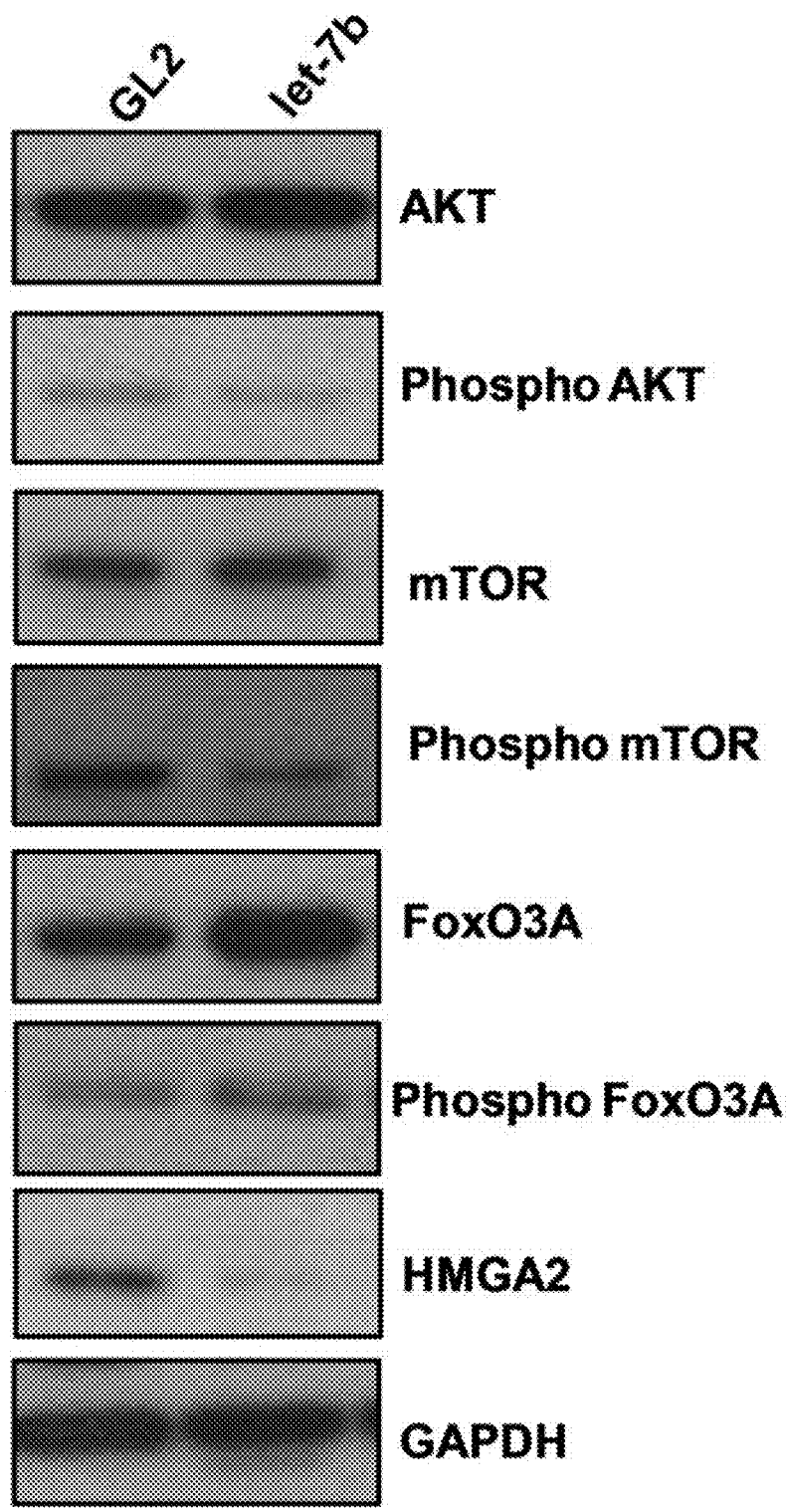
FIG. 8: let-7b induces autophagy by regulating mTORC1 and FoxO3A pathway. Transfection of let-7b decreases AKT activity (phosphor AKT) and in turn decreases mTOR activity (phospho-mTOR) and increases FOX3A transcription and activity (phosphor-FoXO3A).

Several signaling molecules such as PI3, AKT, mTORC1, and FoxO3A regulating autophagy pathway have been established. HMGA2 upregulates IGFBP2 by binding to its 3'UTR. IGFBP2 is an important positive regulator of IGF-1/IGF2 signaling that triggers PI3-AKT signaling cascade. Without wishing to be bound by any particular theory, based on the facts disclosed above, it was hypothesized that let-7b induce autophagy in DR progression through HMGA2/IGFBP2 axis by repressing PI3-AKT signaling cascade and subsequently repressing mTORC1 or inducing FoxO3A pathway. Indeed, the present studies show that let-7b induces autophagy by regulating mTORC1 and FoxO3A pathway. Transfection of let-7b decreases AKT activity (phosphor AKT) and in turn decreases mTOR activity (phospho-mTOR) and increases FOX3A transcription and activity (phosphor-FoXO3A) (FIG. 8).

Overexpression of Let-7b Accelerate the Diabetic Retinal Degeneration.

Figure 9:
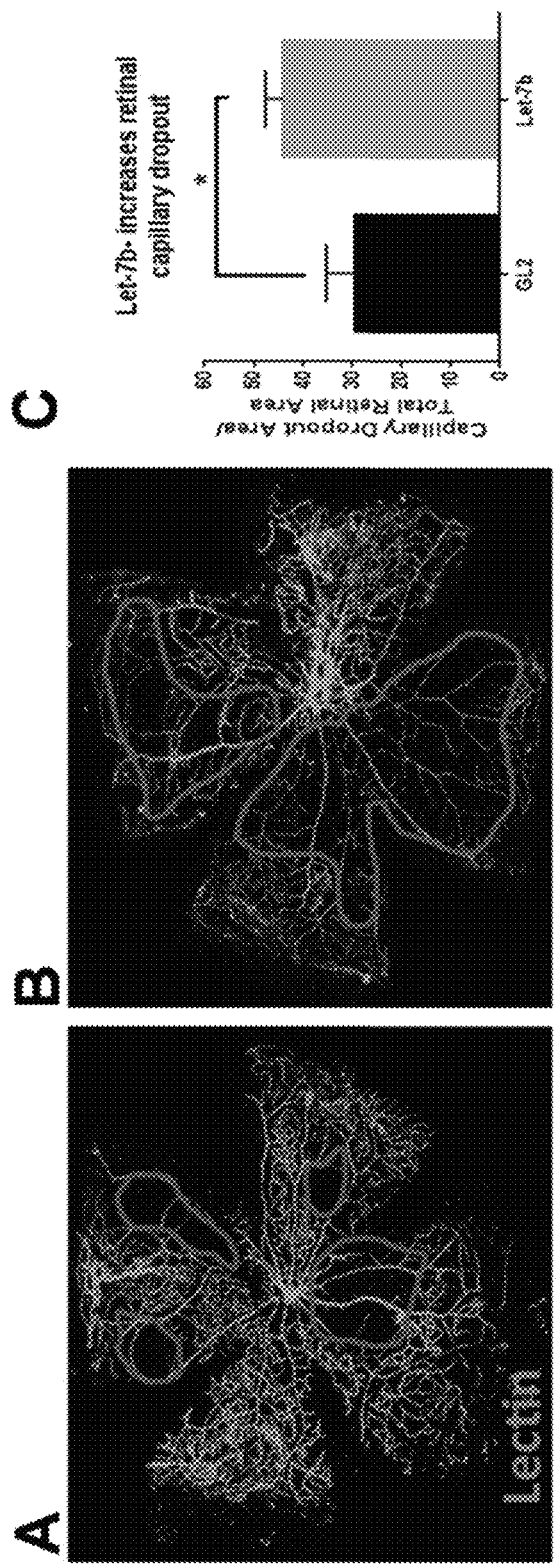
FIG. 9A-C: Overexpression of let-7b accelerates the diabetic retinal degeneration. Intravitreal injection of let-7b into female Akimba mice increases retinal capillary dropout. Please note that female mice provide milder phenotypes as compared to male. Six-week old female Akimba mice (n=6) were injected with let-7b lipid complex in one eye and GL2 control in the contralateral eye. When examined at 10 weeks of age, the let-7b-injected retinas (B) showed more pronounced capillary dropout (circled in red) than control GL2-injected retinas (A). (C) Injection of let-7b significantly increases ($p^* < 0.05$) the ratio of capillary dropout to total retinal area approximately 33% relative to the control GL2 injection.

Intravitreal injection of let-7b into Akimba mice significantly increases the ratio of capillary dropout to total retinal area approximately 33% relative to the control GL2 injection (FIG. 9). Six-week old female Akimba mice (n=6) were injected with let-7b lipid complex in one eye and GL2 control in the contralateral eye. When examined at 10 weeks of age, the let-7b-injected retinas showed more pronounced capillary dropout than control GL2-injected retinas (FIG. 9).

Inhibition of Let-7b Protects the Diabetic Retina.

Figure 10:
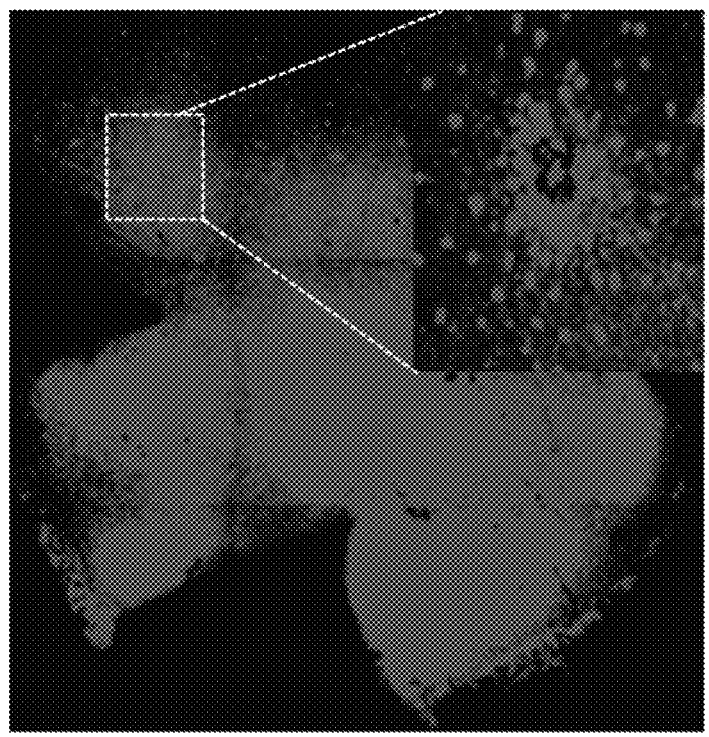
FIG. 10: Intravitreally injected Dy-547 conjugated let-7b inhibitor localizes uniformly in the retinal vasculature (magnification demonstrated in inset).

Next, it was determined whether intravitreally injected let-7b antagomiR can protect against and repair the large-scale loss of retinal vessels and aberrant neovascularization. First, it was demonstrated that let-7b antagomiR localizes uniformly in the retinal vasculature by injecting Dy-547 conjugated let-7b antagomiR (FIG. 10). Six-week old male mice Akimba mice were injected with let-7b antagomiR (ant-let-7b) in the one eye and negative control antagomiR (ant-NC) in the contralateral eye. Intravitreal injection of let-7b antagomiR in Akimba eye at 10 weeks protects retinal cells and vasculature indicating a therapeutic potential for let-7b for advanced stage DR (FIG. 11).

Discussion:

The present studies are the first to functionally investigate the network of microRNAs and key biological pathways that regulate DR and determine their important role in progression of retinal degeneration using retinal perivascular cells and Akimba mouse model. This novel approach, supported by data disclosed herein, is to inhibit let-7b, an important family of microRNAs that will directly control progressive loss of retinal microvasculature to protect against future vision loss in DR. This new paradigm for treatment of DR is normalization of altered microRNAs and, therefore, balancing the microenvironment of the retinal vasculature. This strategy will prevent progressive vessel dropout and prevent eventual vision loss. The approach disclosed herein is supported well by the data provided in the present Examples and Figures. For example, it is disclosed that let-7b is substantially elevated both in Akimba retina and in patients with PDR (FIG. 2) and that inhibition of let-7b by antagomiRs slows progression of retinal degeneration (FIG. 11). These findings strongly support the use of let-7b inhibitors as a new therapeutic strategy for DR.

The data disclosed herein further suggest that chronic hyperglycemia eventually triggers excessive autophagy in retinal cells and vasculature that subsequently leads to massive destruction in the vasculature of advanced DR retina (FIG. 4-6). Autophagy is a self-clearing process that maintains cellular homeostasis and necessary for cellular protection but become destructive when triggered uncontrollably. Aberrant autophagy is associated with numerous human degenerative diseases including age-related macular degeneration, glaucoma, and photoreceptor degeneration. The present application provides data that further support a role for elevated let-7b triggering excessive autophagy in retinal microvasculature that in turn leads to progressive destruction of the retina. On the basis of these evidences, disclosed herein is a mechanism where let-7b regulates autophagy targeting important molecules of the autophagy pathways (FIG. 1, 7, 8).

This work contributes to understanding the basic mechanism of DR progression by elucidating important genetic networks and key biological pathways, and therefore, helping to devise new therapeutic strategies for DR.

Figure 3:
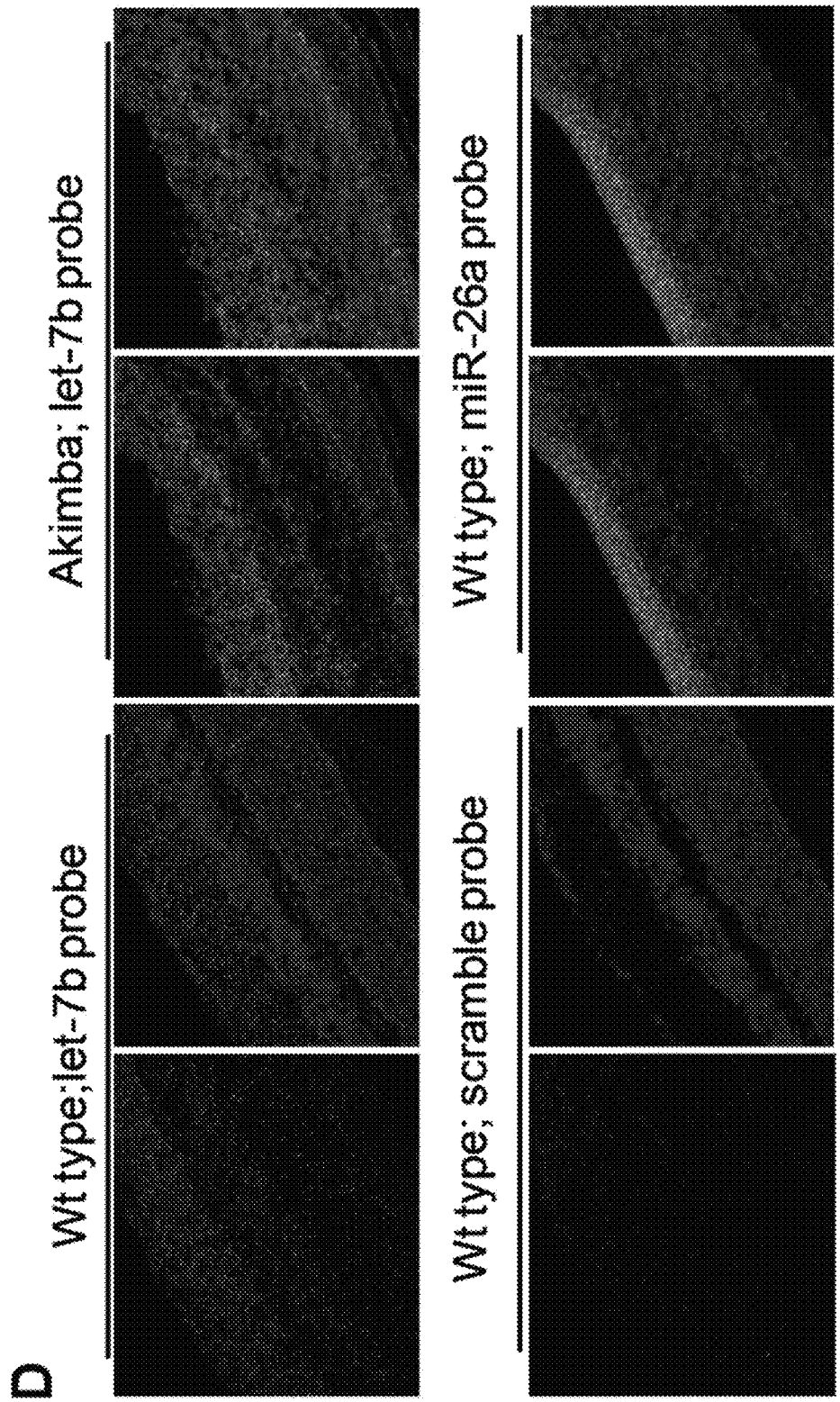
FIG. 3A-D: let-7b expression is upregulated in the retina during diabetic retinopathy of Akimba mouse model. Retinal vasculature of age-matched (A) WT (C57Bl/6J), (B) Akimba DR mouse models. Akimba has extensive capillary dropout and neovascular tufts (arrows) characteristic of advanced stage ischemic DR. Scale bar=100 µm. (C) qRT-PCR showing let-7b is gradually upregulated in Akimba retina. (D) Fluorescence In Situ Hybridization (FISH) of retinal sections reveals increased let-7b (green) expression in Akimba retina vs WT. Expression is most notable in RGC/IPL layers. miR-26a serves as positive control. DAPI is blue.

The numbers of retinal vasculature and support cells are significantly reduced in the Akimba model of DR. It is disclosed herein that microRNA let-7b is dramatically up-regulated in the retinas of these mice (FIG. 3). Using the Akimba model, it was determined that intravitreally injected microRNA let-7b inhibitor (Dy547-mA(*)mA(*)mCmC-mAmCmAmCmAmAmCmCmUmAmCmUmAmCmCmU (*)m C(*)mA (*)(3'-Chl)) can protect against and repair the large-scale loss of retinal vessels and aberrant neovascularization that is similar to what is observed clinically in diabetic patients. The Dy547 is the attached label.

Because the data demonstrate that miRNA let-7b overexpression or levels have an effect and that inducing overexpression or levels or administering miRNA let-7b has similar effects, the present invention encompasses this method for other uses where increased levels of miRNA let-7b are desirable. Furthermore, let-7c-5p and let-7i-5p are also disclosed herein to be overexpressed, suggesting that their inhibition will also be a useful treatment.

Prophetic Examples

Experimental Design:
microRNA let-7b inhibitor-mediated stabilization of retinal vasculature and prevention of neovascularization.

MicroRNA let-7b inhibitor are injected intravitreally in 4-5 week old male Akimba mice (6 mice per group) twice at 2 weeks interval. Mice are examined 1, 3, 6, and 9 months after the second injection. In live animals, fluorescein angiography will be employed to non-invasively assess vessel permeability via dye leakage and the amount of neovascularization. At terminal endpoints retinae will be harvested, and samples will be further analyzed for vasculature and pericyte density, overall morphology and thickness of the retina, as well as molecular analysis for the gene network implicates autophagy pathway (See Examples above).

Output Metrics & Statistics:

The degree of dye leakage will be assessed with a Heidelberg Spectralis Retinal Imager by comparing fluorescein diffusion in early and late time points over the area of neovascularization. Lectin staining will mark vasculature and pericyte markers such as NG2, SMA, and PDGF-B, and morphology will help to quantify perivascular cell numbers. Histochemical analyses will measure the retinal thickness and cell counts. The gene network implicating autophagy pathway and autophagy markers will be analyzed by qPCR, western blotting, and immunohistochemistry.

Expected Results:

Stabilization of neovascularization—We expect to see decreased fluorescein leakage from retinal neovascularization in microRNA-let-7b inhibitor injected retinas. We have already observed protection of vasculature, increased retinal thickness, and increase in cell numbers (See Examples above). We expect that increased vasculature will be accompanied by increased perivascular cell coverage and optimal autophagy function.

We propose to inject microRNA-let-7b inhibitor into the eyes of mice with diabetic retinopathy mouse eye as a treatment to improve the retinal vasculature and other symptoms of retinopathy. This microRNA inhibitor has a unique property in that it is capable of functioning in protecting retinal vascular networks. Our hypothesis is that the microRNA let-7b inhibitor can protect and even improve damaged retinal vessels and thereby helps nourishment of the supporting cells. This can potentially halt progression of diabetic retinopathy of more than 23.6 million US residents who have diabetes.

The disclosures of each and every patent, patent application, and publication cited herein are hereby incorporated by reference in their entirety.

Headings are included herein for reference and to aid in locating certain sections. These headings are not intended to limit the scope of the concepts described therein under, and these concepts may have applicability in other sections throughout the entire specification.

While this invention has been disclosed with reference to specific embodiments, it is apparent that other embodiments and variations of this invention may be devised by others skilled in the art without departing from the true spirit and scope of the invention.

BIBLIOGRAPHY

1. Klein, M. L., W. M. Mauldin, and V. D. Stoumbos, Heredity and age-related macular degeneration. Observations in monozygotic twins. Archives of Ophthalmology, 1994. 112(7): p. 932-7.
2. Janssen, H. L., et al., Treatment of HCV infection by targeting microRNA. N Engl J Med, 2013. 368(18): p. 1685-94.
3. Li, Z. and T. M. Rana, Therapeutic targeting of microRNAs: current status and future challenges. Nat Rev Drug Discov, 2014. 13(8): p. 622-38.
4. Rakoczy, E. P., et al., Characterization of a mouse model of hyperglycemia and retinal neovascularization. Am J Pathol, 2010. 177(5): p. 2659-70.
5. Robinson, R., et al., Update on animal models of diabetic retinopathy: from molecular approaches to mice and higher mammals. Dis Model Mech, 2012. 5(4): p. 444-56.
6. Traktuev, D. O., et al., A population of multipotent CD34-positive adipose stromal cells share pericyte and mesenchymal surface markers, reside in a periendothelial location, and stabilize endothelial networks. Circ Res, 2008. 102(1): p. 77-85.
7. Cunha-Vaz, J. G., Diabetic retinopathy: surrogate outcomes for drug development for diabetic retinopathy. Ophthalmologica, 2000. 214(6): p. 377-80.
8. Motiejunaite, R. and A. Kazlauskas, Pericytes and ocular diseases.
Experimental Eye Research, 2008. 86(2): p. 171-7.

What is claimed is:

1. A method for treating a retinopathy, said method comprising providing a subject suffering from a retinopathy in which stabilization of vasculature in an eye of the subject is desired; and intravitreally administering to the subject a pharmaceutical composition comprising a pharmaceutically acceptable carrier and an effective amount of an inhibitor of micro RNA (miRNA) let-7b levels or activity.

2. The method of claim 1, wherein said inhibitor is a nucleic acid.

3. The method of claim 2, wherein said nucleic acid is an antagomir of miRNA let-7b.

4. The method of claim 2, wherein said nucleic acid comprises the sequence SEQ ID NO:1 or a biologically active homolog or fragment thereof.

5. The method of claim 4, wherein said nucleic acid comprising the sequence SEQ ID NO:1 or a biologically active homolog of fragment thereof is modified.

6. The method of claim 5, wherein said modification is selected from the group consisting of a detectable label, phosphorothioate modification, 2'-O-methyl modification, 2'-O-methoxyethyl modification, 3'-cholesterol (chl) modification, and locked nucleic acid (LNA) modification.

7. The method of claim 5, wherein said nucleic acid comprises at least two modifications.

8. The method of claim 6, wherein said nucleic acid comprises at least one phosphorothioate modification.

9. The method of claim 6, wherein said nucleic acid comprises at least one 2'-O-methyl modification.

10. The method of claim 6, wherein said nucleic acid comprises at least one 2'-O-methoxyethyl modification.

11. The method of claim 6, wherein said nucleic acid comprises a 3'-chl modification.

12. The method of claim 6, wherein said nucleic acid comprises at least one LNA modification.

13. The method of claim 6, wherein said nucleic acid comprises a detectable label.

14. The method of claim 8, wherein said nucleic acid comprises five phosphorothioate modifications.

15. The method of claim 9, wherein said nucleic acid comprises a 2'-O-methyl modification at each nucleotide residue.

16. The method of claim 12, wherein said nucleic acid comprises an LNA at each nucleotide residue.

17. The method of claim 5, wherein said fragment is SEQ ID NO:2 or a modification thereof.

18. The method of claim 1, wherein said inhibitor is selected from the group consisting of Antagomir-let7b which comprises Dy547 mA(*)mA(*)mCmCmAmCmAmCmAmAmCmCmUmAmCmUmAmCmCmU(*)mC(*)mA (*) (3'-Chl), LNA-Chl anti-sense let-7b which comprises IAIAICICIAICIAICIAIAICICIUIAICIUIAICICIUICIA(3'-Chl), LNA anti-sense let-7b which comprises IAIAICICIAICIAICIAIAICICIUIAICIUIAICICIUICIA, MOE anti-sense let-7b which comprises meAmeAmeCmeCmeAmeCmeAmeCmeAmeAmeCmeCmeUmeAmeCmeUmeAmeCme CmeUmeCmeA, Antagomir let-7b mini (truncated version) which comprises mA(*)mA(*)mCmCmAmCmAmCmAmAmCmC(*)mU(*)mA (3'-Chl), LNA-Chl anti-sense let-7b mini which comprises IAIAICICIAICIAICIAIAICICIUIA (3'-Chl), LNA anti-sense let-7b mini which comprises IAIAICICIAICIAICIAIAICICIUIA, and MOE anti-sense let-7b mini which comprises meAmeAmeCmeCmeAmeCmeAmeCmeAmeAmeCmeCmeUmeA, wherein Dy547 is a fluorescent molecule; "m" indicates 2-O-Methyl moiety; * indicates phosphorothioate; (3'-Chl) indicates a cholesterol molecule at the 3'; "I" indicates LNA modification; and "me" indicates 2'-O-methoxyethyl modification.

19. The method of claim 1, wherein said method stimulates vascular stabilization and an increase in retinal thickness.

20. The method of claim 1, wherein said method reduces hyperproliferation of microvascular cells, retinal capillary dropout, and microvascular leakage.

21. The method of claim 1, wherein said retinopathy is diabetic retinopathy.

22. A method for inhibiting the effects of increased levels or activity of miRNA let-7b in a subject in need thereof, wherein said increased levels or activity are associated with a microvasculature injury, disease, or disorder of the eye, said method comprising providing a subject in which stabilization of vasculature in an eye of the subject is desired; and intravitreally administering to said subject a pharmaceutical composition comprising a pharmaceutically acceptable carrier and an effective amount of an inhibitor of miRNA let-7b levels or activity.

23. The method of claim 22, wherein said inhibitor is a nucleic acid comprising the sequence SEQ ID NO:1 or a biologically active homolog or fragment thereof and said sequence is modified.

24. The method of claim 22, wherein said increased levels or activity of miRNA let-7b are associated with diabetic retinopathy.

* * * * *